(12) United States Patent
Konakanchi et al.

(10) Patent No.: US 10,106,554 B2
(45) Date of Patent: Oct. 23, 2018

(54) 7-(MORPHOLINYL)-2-(N-PIPERAZINYL) METHYL THIENO [2, 3-C] PYRIDINE DERIVATIVES AS ANTICANCER DRUGS

(71) Applicant: NATCO PHARMA LIMITED, Hyderabad (IN)

(72) Inventors: Durga Prasad Konakanchi, Hyderabad (IN); Subba Rao Pula, Hyderabad (IN); Rama Krishna Pilli, Hyderabad (IN); Lakshmana Viswa Venkata Pavan Kumar Maddula, Hyderabad (IN); Srinivasa Krishna Murthy Konduri, Hyderabad (IN); Janaki Rama Rao Ravi, Hyderabad (IN); Naga Vasanta Srinivasu Vuppalapati, Hyderabad (IN); Sandeep Kumar Thoota, Hyderabad (IN); Pulla Reddy Muddasani, Hyderabad (IN); Kali Satya Bhujanga Rao Adibhatla, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 15/535,016

(22) PCT Filed: Dec. 11, 2014

(86) PCT No.: PCT/IN2014/000770
§ 371 (c)(1),
(2) Date: Jun. 9, 2017

(87) PCT Pub. No.: WO2016/092556
PCT Pub. Date: Jun. 16, 2016

(65) Prior Publication Data
US 2017/0320891 A1     Nov. 9, 2017

(51) Int. Cl.
*C07D 495/04*     (2006.01)

(52) U.S. Cl.
CPC ................. *C07D 495/04* (2013.01)

(58) Field of Classification Search
CPC .................................................. C07D 495/04
See application file for complete search history.

(56) References Cited

U.S. PATENT DOCUMENTS

| | | | |
|---|---|---|---|
| 3,579,526 A | 5/1971 | Klemm et al. | |
| 6,232,320 B1 | 5/2001 | Stewart et al. | |
| 8,653,089 B2 | 2/2014 | Heald et al. | |
| 2009/0098135 A1 | 4/2009 | Belvin et al. | |
| 2009/0247567 A1 | 10/2009 | Do et al. | |
| 2012/0202785 A1 | 8/2012 | Heald et al. | |

FOREIGN PATENT DOCUMENTS

| | | |
|---|---|---|
| EP | 0292051 A2 | 11/1988 |
| GB | 2010249 A | 6/1979 |
| GB | 2031428 A | 4/1980 |
| JP | 2013-505965 A | 2/2013 |
| WO | 2000/075145 A1 | 12/2000 |
| WO | 2005/110410 A2 | 11/2005 |
| WO | 2007/122410 A1 | 11/2007 |
| WO | 2009/071901 A1 | 6/2009 |
| WO | 2011/041399 A2 | 4/2011 |
| WO | 2011/089400 A1 | 7/2011 |

OTHER PUBLICATIONS

International Search Report, dated Mar. 31, 2015, in connection with corresponding International Application No. PCT/IN2014/000, 2 pages.

*Primary Examiner* — Rebecca L Anderson
(74) *Attorney, Agent, or Firm* — Kilpatrick Townsend & Stockton LLP

(57) ABSTRACT

The present invention relates to novel series of substituted 7-(morpholinyl)-2-(N-piperazinyl)-methyl thieno [2, 3-c] pyridines of the following structure of formula I. Where in R1, R2, R3 and R4 are defined.

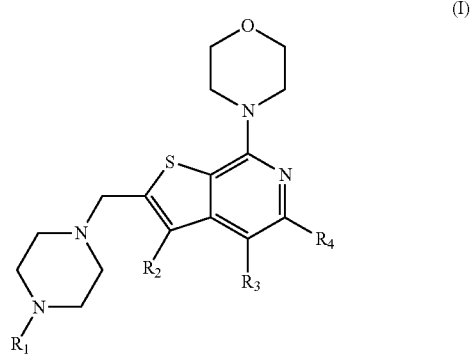

(I)

7 Claims, 2 Drawing Sheets

| Name of the Cell line | Type of cell line | IC Values (nM) | | |
|---|---|---|---|---|
| | | GDC-0941 | Compound 1 | Compound 2 |
| NCI-H292 | Lung cancer | 638 (Lit: 750) | 836 | 643 |
| HCC827 | Lung cancer | 1397 (Lit:1200) | 1708 | 1495 |
| A549 | Lung cancer | 8776 (Lit: 6800) | 3491 | 2009 |
| MDA-MB-361 | Breast cancer | 114 (Lit: 140) | 364 | 151 |
| MDAMB-231 | Breast cancer | >10000(Lit: >10000) | 4033 | 9793 |
| MIAPaCa-2 | Pancreatic cancer | 1766 | 1128 | 1064 |
| PC3 | Prostate cancer | 1048 | 1439 | 1060 |
| U-87 | Glioma | >10000 | 5349 | 10000 |

Figure-1: Anti-proliferative activity of compound-1 & 2 on various solid tumor cell lines

| S. No. | Group | No. of animals | Initial tumor volume (Mean ± SEM) | Tumor volume after treatment (Mean ± SEM) | | | |
|---|---|---|---|---|---|---|---|
| | | | | 3$^{rd}$ Day | 7$^{th}$ Day | 15$^{th}$ Day | 23$^{rd}$ Day |
| I | Control (Vehicle) (2% Gum acacia + 2% SLS) | 5 | 273.84 ± 77.35 | 325.04 ± 63.56 | 507.48 ± 61.10 | 1020.8 ± 190.96 | 2098.8 ± 174.34 |
| II | Compound 2 (200 mg/kg, p.o) | 5 | 398.39 ± 53.20 | 355.95 ± 43.13 | 240.90 ± 22.83 | 116.41 ± 21.98 | 35.13 ± 2.07*** |
| III | Compound 1 (50 mg/kg, p.o) | 5 | 421.27 ± 113.24 | 387.16 ± 102.90 | 280.22 ± 76.03 | 130.82 ± 55.19 | 40.13 ± 31.89*** |
| IV | Standard [Erlotinib (50 mg/kg, p.o) + Gemcitabine (120 mg/kg, i.p)] | 5 | 342.47 ± 64.06 | 322.57 ± 49.75 | 194.58 ± 27.56 | 86.28 ± 18.23 | 20.72 ± 8.91*** |

Figure 2: Anti-tumor activity of COMPOUND 1 and COMPOUND 2 against tumor induced by pancreatic cell Line MIAPaca-2 in nude mice

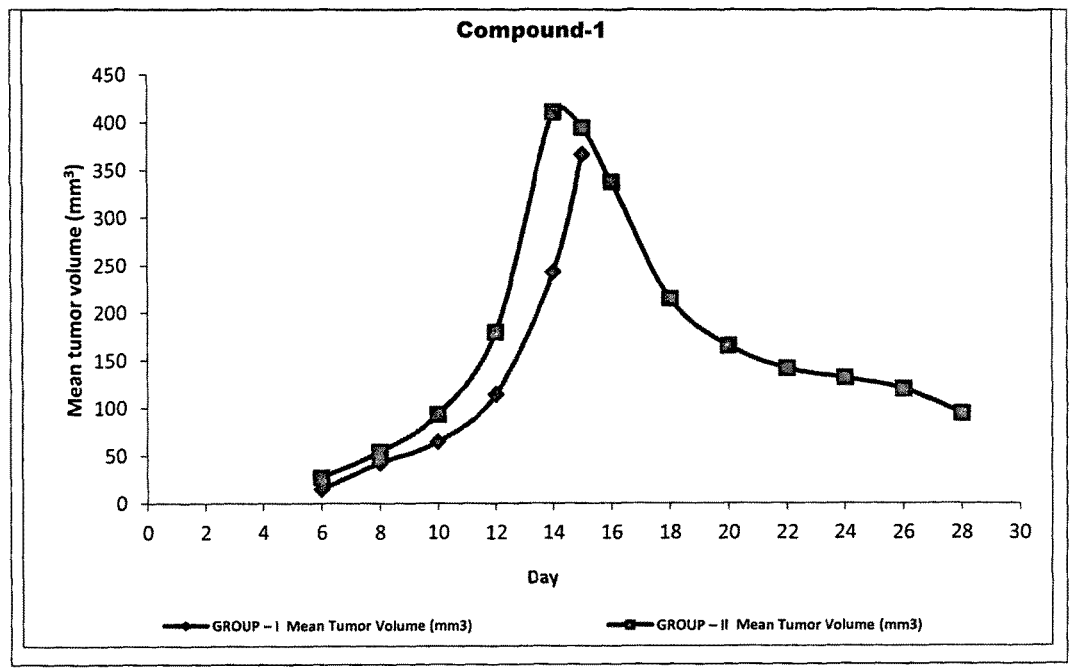
Figure 3: Anti-tumor activity of COMPOUND 1 against tumor induced by NCI-H292 (Lung cancer/ Erlotinib resistant)
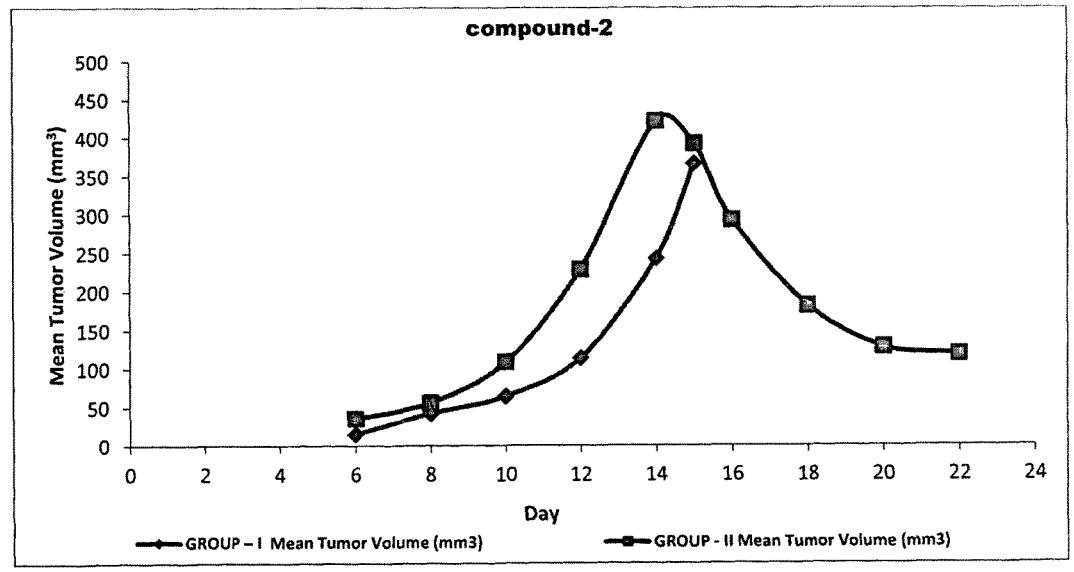
Figure 4: Anti-tumor activity of COMPOUND 2 against tumor induced by NCI-H292 (Lung cancer/Erlotinib resistant)

7-(MORPHOLINYL)-2-(N-PIPERAZINYL) METHYL THIENO [2, 3-C] PYRIDINE DERIVATIVES AS ANTICANCER DRUGS

CROSS-REFERENCE TO RELATED APPLICATIONS

This application is a national phase application under 35 U.S.C. 371 claiming priority to PCT/IN2014/000770, filed Dec. 11, 2014, the teachings of which are hereby incorporated by reference in their entireties for all purposes.

FIELD OF INVENTION

The present invention relates to a series of novel substituted 7-(morpholinyl)-2-(N-piperazinyl)-methyl thieno [2, 3-c] pyridines which are useful in treating various cancers of the brain, breast, lung, pancreatic and prostate and the like. The present invention provides a series of novel substituted 7-(morpholinyl)-2-(N-piperazinyl)-methyl thieno [2, 3-c] pyridines of formula I, or a pharmaceutically acceptable salt thereof,

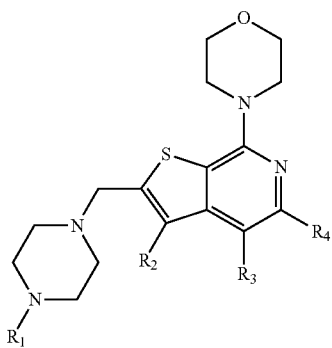

Formula I

Wherein

R1 can be —H, —C1-C6 alkyl, —C3-C6 cycloalkyl, —C(O)R5, —S(O)$_2$R5, —C(O)$_2$R5, —C1-C6 alkyl substituted with R6, —C3-C6 cycloalkyl substituted with R6, -aryl, -aryl substituted with R6, -heteroaryl groups substituted with R6, etc.

R2, R3 and R4 can independently be —H, —OH, —SH, -halo, -amino, -cyano, nitro, —C1-C6 alkyl, —C3-C6 cycloalkyl, -aryl, -lower alkoxy group, —C(O)R5, —S(O)$_2$R5, —C(O)$_2$R5, —C≡C—R6, -aminocarbonyl substituted with R6, -alkylamino group substituted either with R6 or optionally containing —C3-C6 cycloalkyl, alkylaminocarbonyl, -arylaminocarbonyl, heteroaryl, substituted heteroaryl optionally substituted with either H, amino, aminoalkyl or aminocycloalkyl containing C3—C6 carbon atoms, fused bicyclic or tricyclic heteroaryl containing 1,2 or 3 heteroatoms such as N, O, S, substituted aryl group optionally substituted with either hydroxyl, hydroxyl alkyl, amino, aminoalkyl, amino carbonyl, alkynyl, cyano, halogen, loweralkoxy, or aryloxy, or optionally substituted with R6 etc.

R5 can be —H, -alkyl, amino, -aminoalkyl, —N(alk)$_2$, -aryl substituted with R6, hetero aryl substituted with R6, -fused heteroaryl substituted with R6, -trifluoromethyl, etc.

R6 can be selected from —H, hydroxy, halogen, cyano, nitro, amino, —C1-C6 alkyl, —N(alk)$_2$, -substituted alkyl (CH)$_{0-6}$, -optionally substituted aryl, -an optionally substituted heteroaryl, -an optionally substituted aralkyloxy, -an aryl(hydroxyl) alkyl, -an aromatic acyl amino, -an arylsulfonylamino, -a lower alkoxyl aryl sulfonylamino, -a hydroxyl lower alkoxyl styryl, -lower alkoxyl aryloxy, -an optionally substituted arylalkenyl, -heteroarylalkenyl, -heteroarylalkynyl, -aromatic acyl alkynyl, -optionally N-substituted amino lower alkyl, -arylamino, -arylalkylamino etc.

BACKGROUND OF THE INVENTION

PCT application WO 2007/122410 certain thieno [2, 3-c] pyrimidine compounds working by PI3 kinase mechanism and useful in treating various proliferative disorders of the brain, breast, lung etc. The structure of lead compound GDC-0941, now called as Pictilisib, is given below:

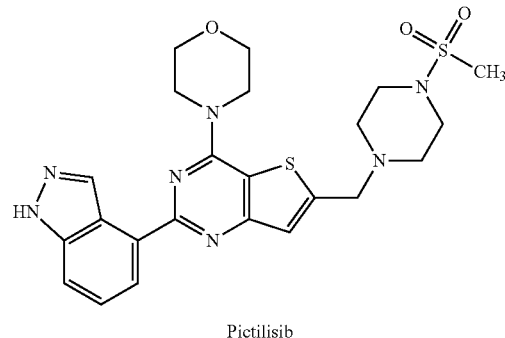 [SMILES: CS(=O)(=O)N1CCN(Cc2cc3nc(-c4cccc5[nH]ncc45)nc(N4CCOCC4)c3s2)CC1]

Pictilisib

Certain thieno [2, 3-c] pyridines as PI3 kinases

WO2009071901A1 is describes a class of fused tricyclic triazole and thiophene derivatives as PI3 kinase inhibitors, which are beneficial in the treatment of inflammatory, autoimmune, cardiovascular, neurodegerative, metabolic, oncological, nociceptive or ophthalmic disordres.

US patent application no. 20090247567A1, describes certain thieno [2,3-c] pyridines, fused benzopyran and fused benzoxipen as PI3 kinase inhibitors.

U.S. Pat. No. 8,653,089 describes as a preparation of heterocyclic compounds as selective inhibitors of the p110 delta isoforms of PI3 kinase for treating inflammation, immune diseases and certain forms of cancers.

Thieno [2,3-c]pyridines for other Applications

U.S. Pat. No. 3,579,526A is describes a series of thienopyridines compounds as useful dye intermediates, insecticides, herbicides, pesticides and lubricating oil additives.

GB2010249A is describes certain thieno [2,3-c]-[3.2-c] pyridines and their therapeutic applications as inflammation inhibitors.

GB2031428A describes new thieno [2,3-c] pyridine derivatives and their therapeutic applications as anti-inflammatory compounds.

EP0292051A2 describes preparation of 2-[(thienopyridinylmethyl) thio] benzimidazoles as antiulcer agents. These benzimidazole and thienopyridine derivatives are excellent antiulcer agents.

WO2000075145A1 and U.S. Pat. No. 6,232,320 describe preparation of thienopyridines and thienopyrimidines as cell adhesion-inhibiting anti-inflammatory compounds.

WO2005110410A2 describes preparation of fused heterocyclic as kinase inhibitors. This invention provides compounds or pharmaceutically acceptable salts as inhibitors of kinases, particularly COT or MK2 kinases.

Present Invention

The main objective of the present invention is to provide a series of novel substituted 7-(morpholinyl)-2-(N-piperazinyl)-methylthieno [2, 3-c] pyridines of general formula I defined above, or their pharmaceutically acceptable salts thereof.

Another objective of the present invention is to provide a series of novel substituted 7-(morpholinyl)-2-(N-piperazinyl)-methylthieno[2,3-c] pyridines of general formula I defined above and their pharmaceutically acceptable salts which are potent and selective PI3 kinase inhibitors and are therefore beneficial in the treatment and prevention of various human ailments such as cancer.

Yet another objective of the present invention is to provide a novel series of substituted 7-(morpholinyl)-2-(N-piperazinyl)-methylthieno [2,3-c]pyridines of general formula I defined above and their pharmaceutically acceptable salts having excellent in-vivo activity against solid tumors such as lung, pancreatic etc.

Another objective of the present invention is to provide a process for the preparation of a series of novel substituted 7-(morpholinyl)-2-(N-piperazinyl)-methylthieno [2, 3-c] pyridines of general formula I defined above and their pharmaceutically acceptable salts.

BRIEF DESCRIPTION OF THE DRAWINGS

FIG. 1: Anti-proliferative activity of compound-1 & 2 on various solid tumor cell lines FIG. 2: Anti-tumor activity of COMPOUND 1 and COMPOUND 2 against tumor induced by pancreatic cell Line MIAPaca-2 in nude mice FIG. 3: Anti-tumor activity of COMPOUND 1 against tumor induced by NCI-H292 (Lung cancer/Erlotinib resistant)

FIG. 4: Anti-tumor activity of COMPOUND 2 against tumor induced by NCI-H292 (Lung cancer/Erlotinib resistant)

DETAILED DESCRIPTION OF THE INVENTION

The compounds in accordance with the present invention, being potent and selective PI3 kinase inhibitors are therefore beneficial in the treatment and prevention of various human ailments such as cancer.

The present invention relates to compounds of formula-I and pharmaceutically acceptable salts thereof, may be prepared by any process known to be applicable to the chemically related compounds.

The invention relates to novel substituted 7-(morpholinyl)-2-(N-piperazinyl) methyl thieno [2, 3-c] pyridines of the formula-I,

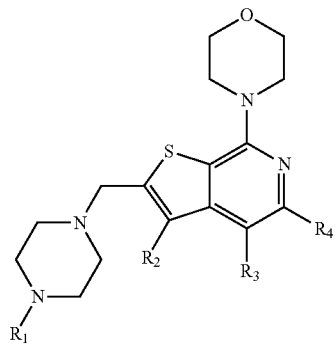

Wherein

R1 can be —H, —C1-C6 alkyl, —C3-C6 cycloalkyl, —C(O)R5,—S(O)$_2$R5,—C(O)$_2$R5, —C1-C6 alkyl substituted with R6, —C3-C6 cycloalkyl substituted with R6, -aryl, -aryl substituted with R6, -heteroaryl groups substituted with R6, etc.

R2, R3 and R4 can independently be —H, —OH, —SH, -halo, -amino, -cyano, nitro, —C1-C6 alkyl, —C3-C6 cycloalkyl, -aryl, -lower alkoxy group, —C(O)R5, —S(O)$_2$R5,—C(O)$_2$R5, —C=C—R6, -aminocarbonyl substituted with R6, -alkylamino group substituted either with R6 or optionally containing —C3-C6 cycloalkyl, alkylaminocarbonyl, -arylaminocarbonyl, heteroaryl, substituted heteroaryl optionally substituted with either H, amino, aminoalkyl or aminocycloalkyl containing C3-C6 carbon atoms, fused bicyclic or tricyclic heteroaryl containing 1,2 or 3 heteroatoms such as N, O, S, substituted aryl group optionally substituted with either hydroxyl, hydroxyl alkyl, amino, aminoalkyl, amino carbonyl, alkynyl, cyano, halogen, lower alkoxy, or aryloxy, or optionally substituted with R6 etc.

R5 can be —H, -alkyl, amino, -aminoalkyl, —N(alk)$_2$, -aryl substituted with R6, hetero aryl substituted with R6, -fused heteroaryl substituted with R6, -trifluoromethyl, etc.

R6 can be selected from —H, hydroxy, halogen, cyano, nitro, amino, —C1-C6 alkyl, —N(alk)$_2$, -substituted alkyl (CH)$_{0-6}$, -optionally substituted aryl, -an optionally substituted heteroaryl, -an optionally substituted aralkyloxy, -an aryl(hydroxyl) alkyl, -an aromatic acyl amino, -an arylsulfonylamino, -a lower alkoxyl aryl sulfonylamino, -a hydroxyl lower alkoxyl styryl, -lower alkoxyl aryloxy, -an optionally substituted arylalkenyl, -heteroarylalkenyl, -heteroarylalkynyl, -aromatic acyl alkynyl, -optionally N-substituted amino lower alkyl, -arylamino, -arylalkylamino etc.

Compounds of formula-I and pharmaceutically acceptable salts thereof may be prepared by any process known to be applicable to the chemically related compounds.

In general the active compounds may be made from the appropriate substituted 7-(morpholinyl)- 2-(N-piperazinyl) methyl-thieno[2,3-c]pyridine compounds derived from the predecessors substituted thieno[2,3-c]pyridines derivatives.

The active compounds of present invention can be prepared by the following synthetic Scheme-I.

Scheme -1

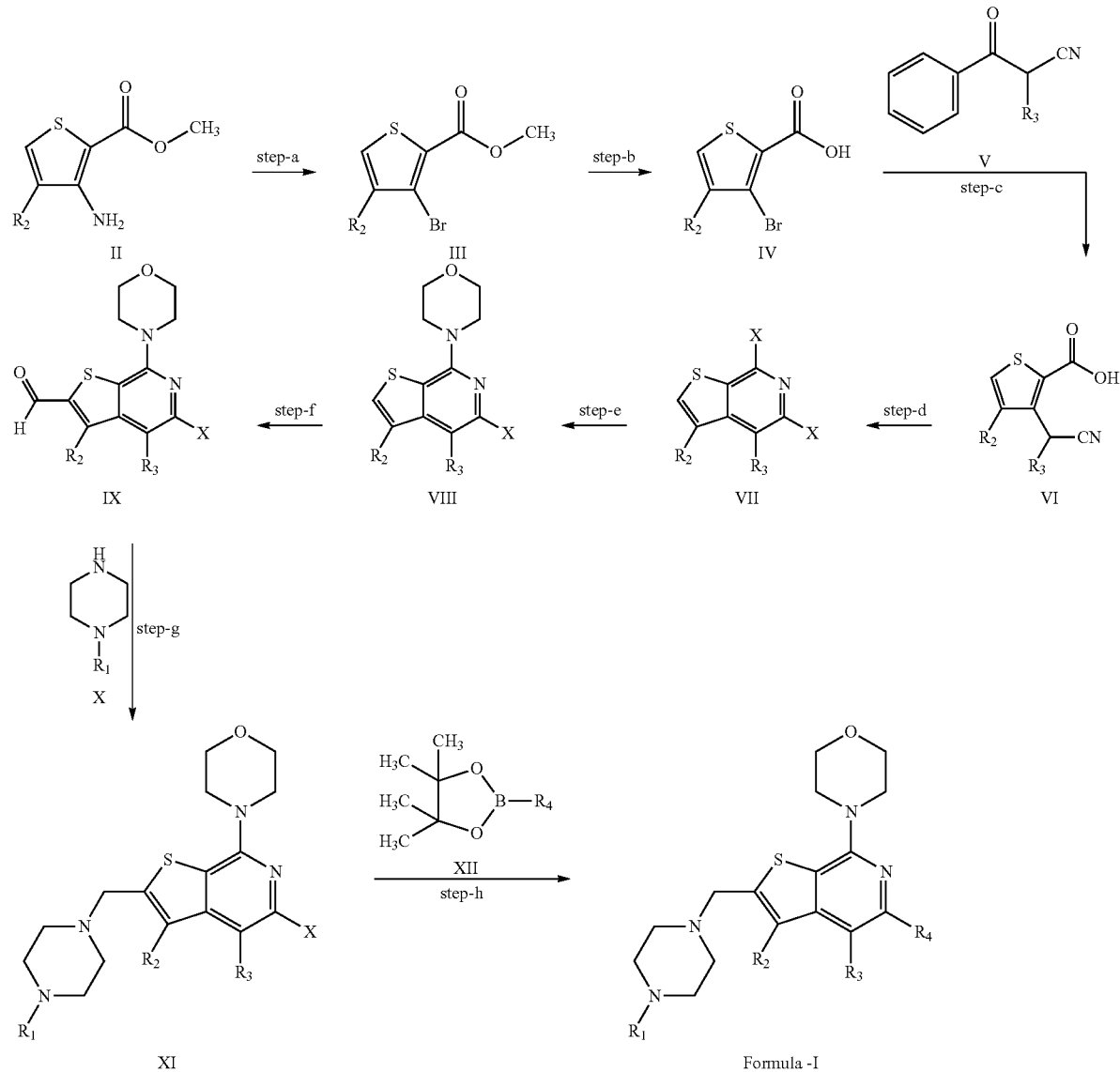

Wherein R1, R2, R3 and R4 are defined as above.
Various Compounds of Formula-I are Prepared by the Following Methods a) Preparation of Formula-III

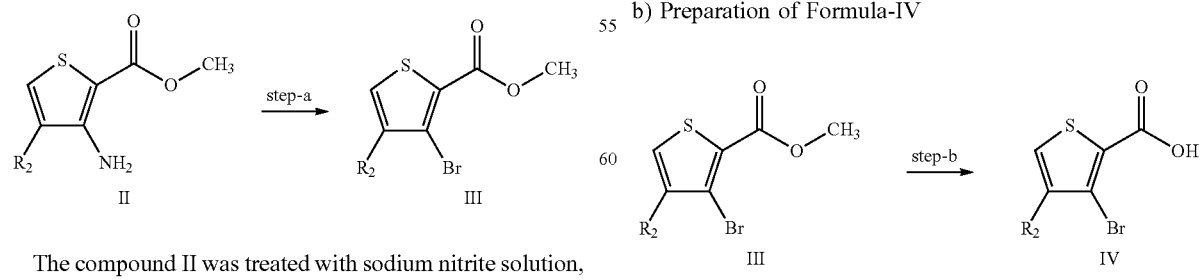

The compound II was treated with sodium nitrite solution, in presence of hydrobromic acid and diazotized solution was slowly added to copper (I) bromide obtained to formula III. Wherein $R_2$ is defined as above. The halogenating agent can be aqueous hydrobromic acid, hydrobromic acid in acetic acid, hydrochloric acid. The reaction can be performed either neatly without any solvent or with hydrobromic acid, DM water etc. The temperature of the reaction maintained between —5° C. to 110° C., preferably the reflux temperature of halogenating reagent.

b) Preparation of Formula-IV

The ester group of compounds of formula-III was hydrolyzed to carboxylic acid derivatives of compounds of formula-III. The formula III compounds were treated with sodium hydroxide solution in presence of tetrahydrofuran, methanol and water. Finally acidified with hydrochloric acid to obtain formula IV (wherein R2 is defined as above). The temperature of the reaction was maintained between 5° C. to 110° C., preferably, between 25° C. to 35° C.

c) Preparation of Formula-VI

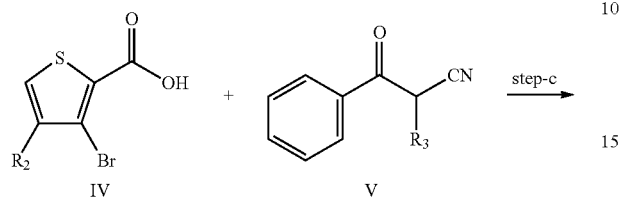

With cyanating agents such as substituted benzoyl acetonitrile in presence of sodium alkoxide and lower alcohol as solvent, or in presence of water, hydrochloric acid etc., and the compounds of formula-IV were converted to cyanomethyl derivatives of thiophene of formula-VI (wherein R2 is defined as above). The temperature of the reaction was maintained between 5° C. to 110° C., preferably the reflux temperature of solvent.

d) Preparation of Formula-VII

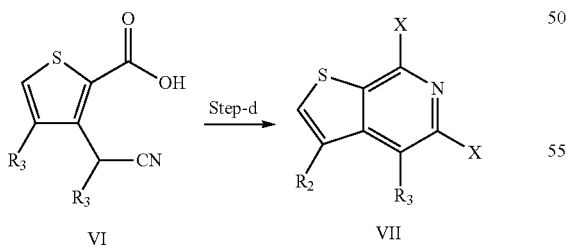

The formula VI compounds were treated with phosphorous trihalide, with catalytic quantity of dimethylformamide, neatly or in presence of solvents such as halogenated aryl or alkanes to obtain compounds of formula-VII (wherein R2, R3 and X are defined as above). The temperature of the reaction was maintained between 25° C. to 180° C., preferably 120° C. to 125° C.

e) Preparation of Formula-VIII

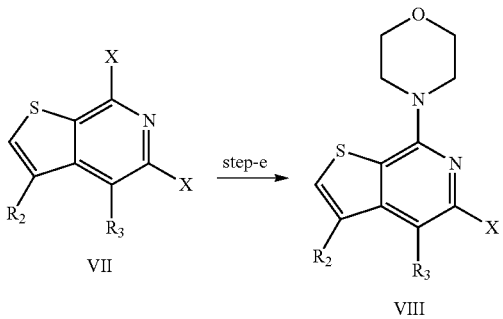

The formula VII compounds were treated with morpholine and ethanol to obtain compounds of formula VIII (wherein R2, R3 and X are defined as above). The temperature of the reaction was maintained between 25° C. to 140° C., preferably 105° C. to 110° C.

f) Preparation of Formula-IX

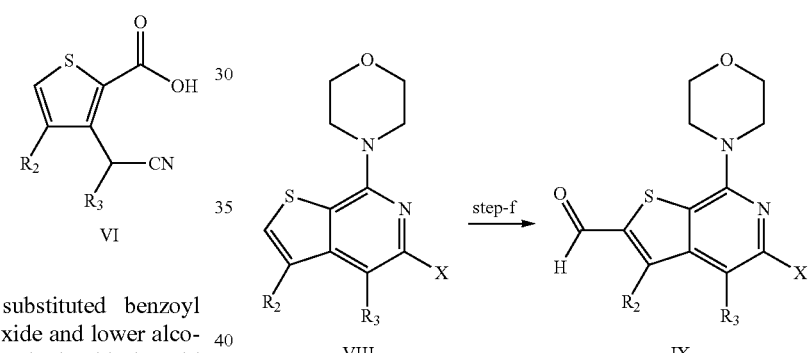

The compounds of formula-VIII were treated with n-butyl lithium in hexane and dimethyl formamide to obtain compounds of formula IX (wherein R2, R3 and X are defined as above). The temperature of the reaction was maintained between −80° C. to 0° C., preferably −60° C. to −70° C.

g) Preparation of Formula-XI

-continued

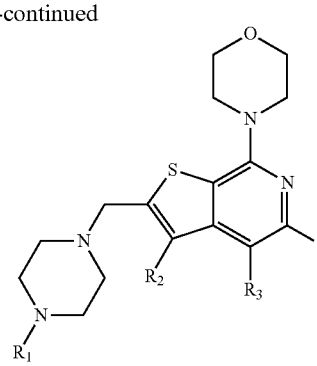

XI

The compounds of formula IX were treated with formula X and trimethyl orthoformate, sodium triacetoxy borohydride to obtain compounds of formula XI (wherein R1, R2, R3, and X are defined as above). The temperature of the reaction was maintained between 0° C. to 110° C., preferably at 25° C. to 35° C.

h) Preparation of Formula-I

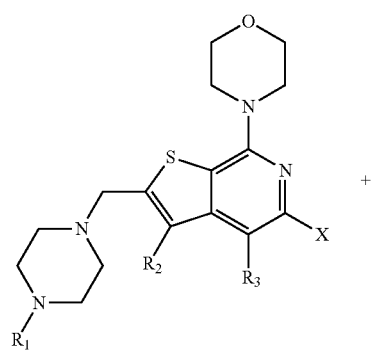

XI

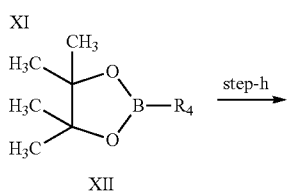

XII step-h

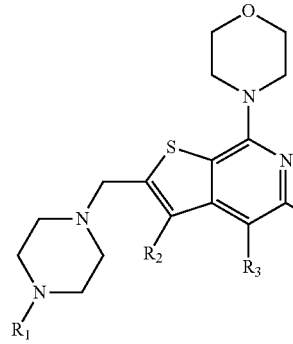

Formula-I

The compounds of formula XI were treated with formula XII of boronic esters or boronic acids in presence of bis triphenylphosphine (II) dichloride, aqueous sodium carbonate solution and toluene and ethanol to obtain compounds of formula I (wherein R1, R2, R3 and R4 are defined as above).

The temperature of the reaction was maintained between 0° C. to 160° C., preferably 115° C. to 120° C.

Alternatively the compounds of formula-XVII can be prepared by the following Scheme-II:

Scheme-II

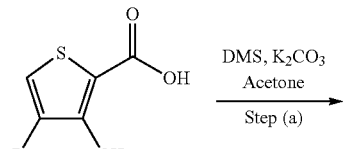

XIII

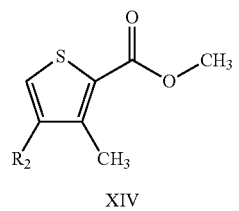

XIV

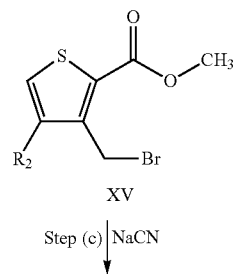

XV

Step (c) | NaCN

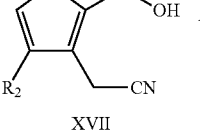 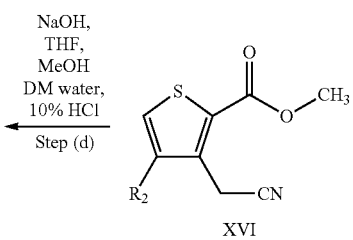

XVII    XVI i) Preparation of Compounds of Formula-XIV

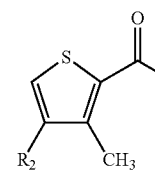 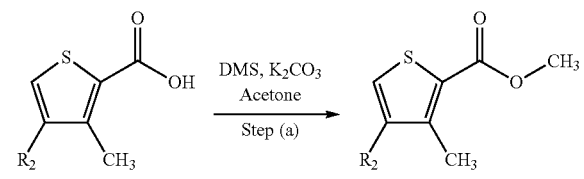

XIII    XIV

The substituted 3-methyl-2-thiophene carboxylic acids (of formula-XIII) were treated with dimethyl sulfate and potassium carbonate in acetone solvent to obtain compounds of formula -XIV. The temperature of the reaction was maintained between 15° C. to 55° C., preferably 25° C. to 30° C.

j) Preparation of Compounds of Formula-XV

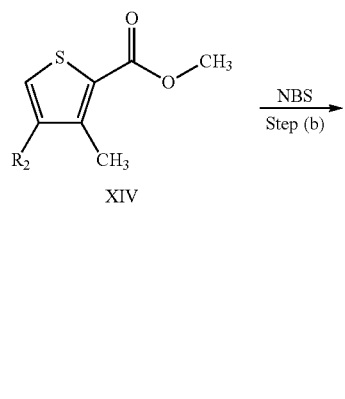

The compounds of formula-XIV were treated with N-bromosuccinimide and benzoyl peroxide in carbon tetrachloride solvent to obtain compounds of formula-XV. The temperature of the reaction was maintained between 25° C. and 110° C., preferably at 40° C. to 80° C. and more preferably at 75° C. to 80° C.

k) Preparation of Compounds of Formula-XVI

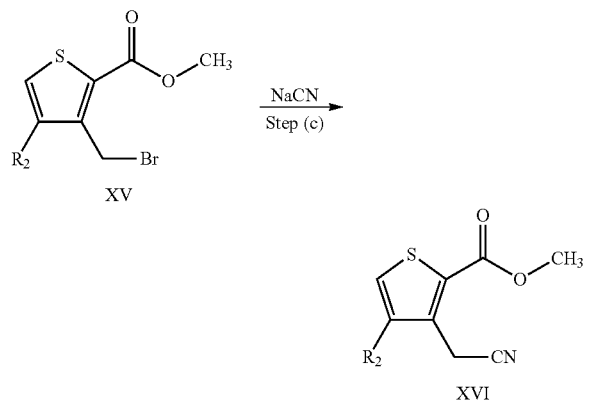

The formula-XV compounds were treated with sodium cyanide in water to obtain compounds of formula-XVI. The temperature of the reaction maintained between 25° C. and 90° C., preferably at 50° C. to 55° C.

l) Preparation of Compounds of Formula-XVII

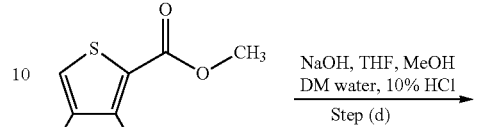

The compounds of formula XVI were treated with sodium hydroxide solution in presence of tetrahydrofuran and methanol and finally acidified with hydrochloric acid solution obtained to Formula -XVII. The temperature of the reaction was maintained between 25° C. and 60° C., preferably at 25° C. to 30° C.

The invention most particularly relates to synthesized novel fused pyridine derivatives as anti-cancer drugs.

| S. No. | Compound number | Structure | Chemical name |
|---|---|---|---|
| 1. | Compound-1 | 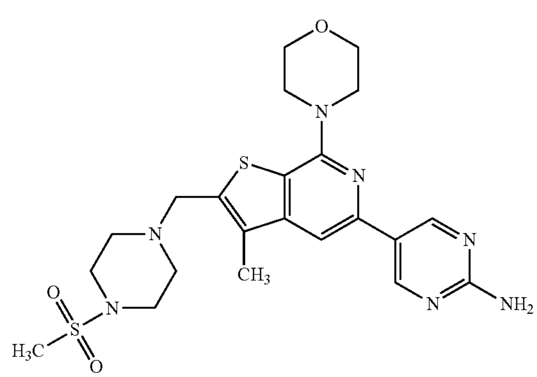 [SMILES: Cc1c(CN2CCN(S(C)(=O)=O)CC2)sc2c(N3CCOCC3)nc(-c3cnc(N)nc3)cc12] | 5-[3-methyl-2-[(4-methyl sulfonylpiperazin-1-yl) methyl]-7-morpholino-thieno[2,3-c]pyridin-5-yl]pyrimidin-2-amine |

-continued

| S. No. | Compound number | Structure | Chemical name |
|---|---|---|---|
| 2. | Compound-2 | 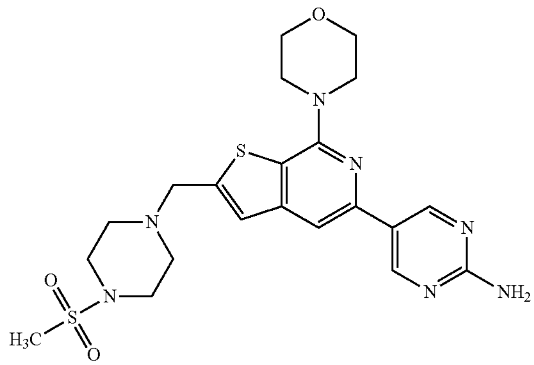 [SMILES: CS(=O)(=O)N1CCN(Cc2cc3cc(-c4cnc(N)nc4)nc(N4CCOCC4)c3s2)CC1] | 5-[2-[(4-methylsulfonyl piperazin-1-yl)methyl]-7-morpholino-thieno[2,3-c]pyridin-5-yl]pyrimidin-2-amine |
| 3. | Compound-3 | 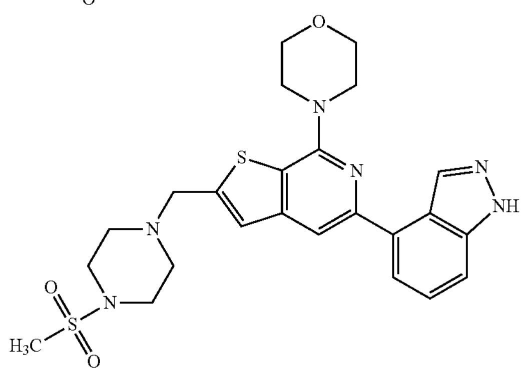 | 4-[5-(1H-indazol-4-yl)-2-[(4-methylsulfonyl piperazin-1-yl)methyl]thieno[2,3-c]pyridin-7-yl]morpholine |
| 4. | Compound-4 | 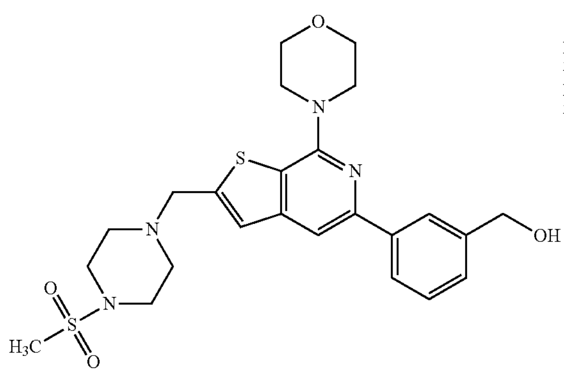 [SMILES: CS(=O)(=O)N1CCN(Cc2cc3cc(-c4cccc(CO)c4)nc(N4CCOCC4)c3s2)CC1] | [3-[2-[(4-methylsulfonyl piperazin-1-yl)methyl]-7-morpholino-thieno[2,3-c]pyridin-5-yl]phenyl]methanol |
| 5. | Compound-5 | 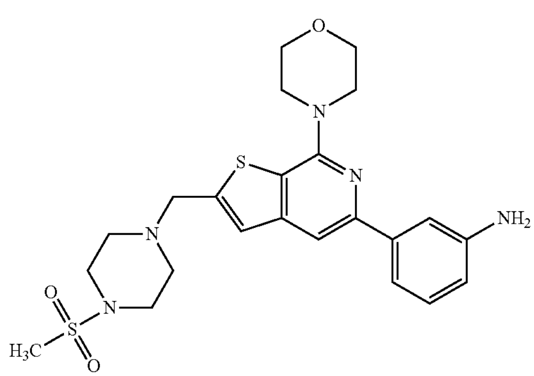 [SMILES: CS(=O)(=O)N1CCN(Cc2cc3cc(-c4cccc(N)c4)nc(N4CCOCC4)c3s2)CC1] | 3-[2-[(4-methylsulfonyl piperazin-1-yl)methyl]-7-morpholino-thieno[2,3-c]pyridin-5-yl]aniline |

-continued

| S. No. | Compound number | Structure | Chemical name |
|---|---|---|---|
| 6. | Compound-6 | 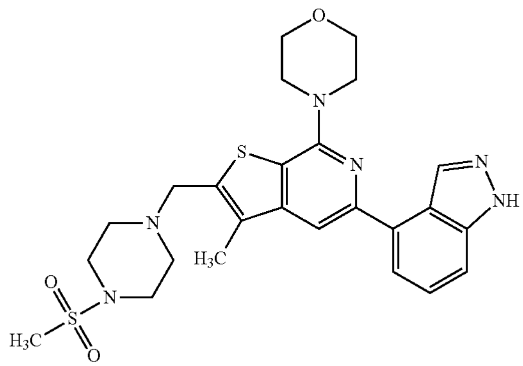 [SMILES: Cc1c(CN2CCN(S(C)(=O)=O)CC2)sc2c(N3CCOCC3)nc(-c3cccc4[nH]ncc34)cc12] | 4-[5-(1H-indazol-4-yl)-3-methyl-2-[(4-methylsulfonyl piperazin-1-yl)methyl]thieno[2,3-c]pyridin-7-yl]morpholine |
| 7. | Compound-7 | 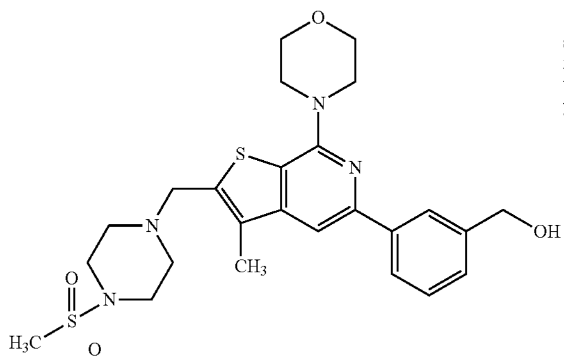 | [3-[3-methyl-2-[(4-methyl sulfonylpiperazin-1-yl) methyl]-7-morpholino-thieno[2,3-c]pyridin-5-yl]phenyl]methanol |
| 8. | Compound-8 | 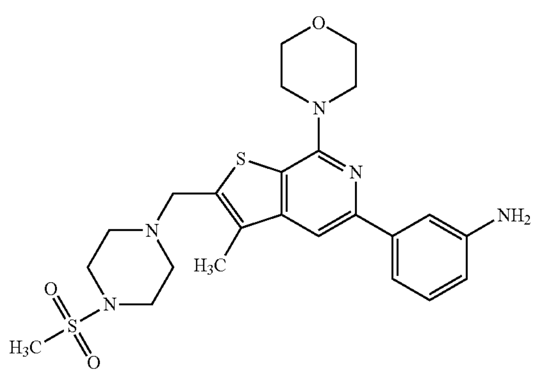 [SMILES: Cc1c(CN2CCN(S(C)(=O)=O)CC2)sc2c(N3CCOCC3)nc(-c3cccc(N)c3)cc12] | 3-[3-methyl-2-[(4-methyl sulfonylpiperazin-1-yl) methyl]-7-morpholino-thieno[2,3-c]pyridin-5-yl]aniline |
| 9. | Compound-9 | 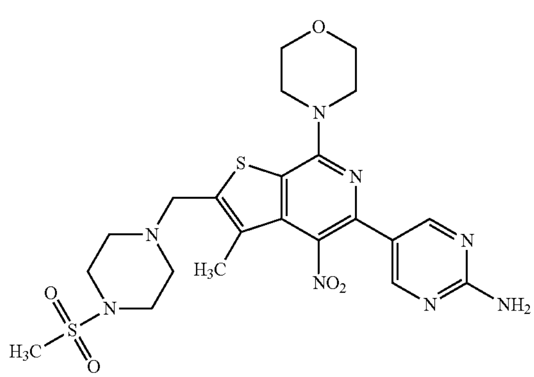 | 5-[3-methyl-2-[(4-methylsulfonylpiperazin-1-yl)methyl]-7-morpholino-4-nitro-thieno[2,3-c]pyridin-5-yl]pyrimidin-2-amine |

| S. No. | Compound number | Structure | Chemical name |
|---|---|---|---|
| 10. | Compound-10 | 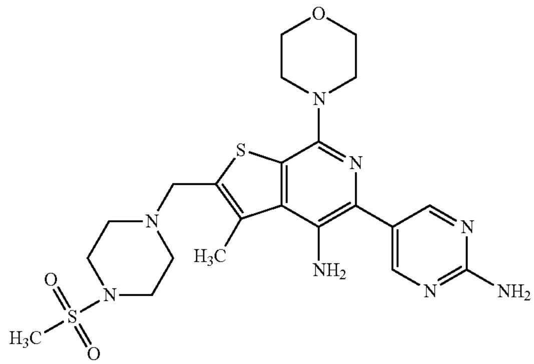 [SMILES: Cc1c(CN2CCN(S(C)(=O)=O)CC2)sc2c(N3CCOCC3)nc(-c3cnc(N)nc3)c([N+](=O)[O-])c12] | 5-(2-amino-pyrimidin-5-yl)-3-methyl-2-[(4-methylsulfonyl piperazin-1-yl)methyl]-7-morpholino-thieno[2,3-c]pyridin-4-amine |
| 11. | Compound-11 | 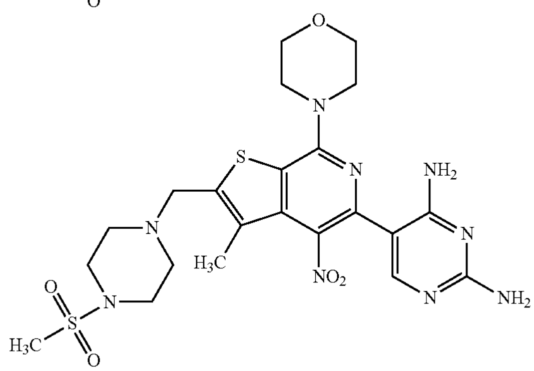 | 5-[3-methyl-2-[(4-methylsulfonylpiperazin-1-yl)methyl]-7-morpholino-4-nitro-thieno[2,3-c]pyridin-5-yl]pyrimidine-2,4-diamine |
| 12. | Compound-12 | 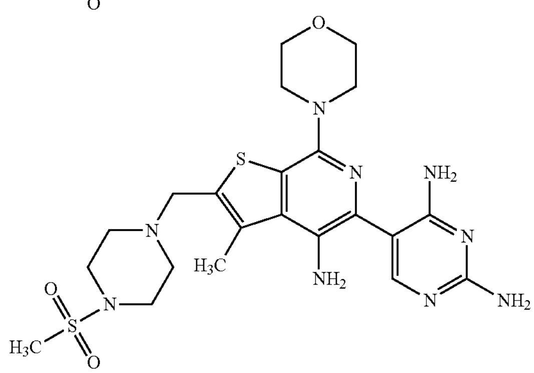 | 5-[4-amino-3-methyl-2-[(4-methylsulfonyl piperazin-1-yl)methyl]-7-morpholino-thieno[2,3-c]pyridin-5-yl]pyrimidine-2,4-diamine |

The details of the invention are given in the examples given below which are provided for illustration only and therefore these examples should not be construed to limit the scope of the invention.

EXAMPLE-1

Preparation of methyl 3-bromo-4-methyl-2-thiophenecarboxylate

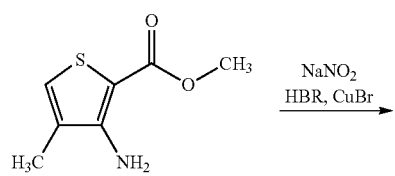

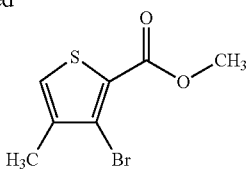

To a stirred solution of 50 g (0.292 mol) of methyl 3-amino-4-methylthiophene-2-carboxylate in 110 ml of hydrobromic acid was added drop wise of 21.17 g (0.306 mol) of sodium nitrite in 50 ml of water, while maintaining the temperature of the reaction mixture at 0-5° C. by cooling in ice-water bath. When the addition was complete, the solution was stirred at 0-5° C. for 60 min. The diazotized solution was added drop wise to a solution of 44.0 g (0.306 mol) of copper (I) bromide in 130 ml of hydrobromic acid, while maintaining the temperature of the reaction mixture at 0-5° C. by cooling in ice-water bath. When the addition was complete, the solution was stirred at 0-5° C. for 30 min and then reaction mixture was heated in a constant-temperature bath at 65° C. The reaction mixture was diluted with 600 ml of water while maintaining at 25-30° C. by cooling and extracted with two 400 ml portions of ethyl acetate. The ethyl acetate extracts were combined, washed two times with 400 ml portions of water, and dried over anhydrous sodium sulfate. The ethyl acetate was removed by distillation under vacuum at 60° C. to give methyl 3-bromo-4-methyl-2-thiophenecarboxylate, 65.5 g (95.3%) as a yellow solid, melting point 73° C. to 76.5° C. with 86% purity by HPLC. $^1$HNMR (400 MHz, DMSO-d$_6$) δ-Value (ppm): 2.21 (d, CH$_3$, 3H), 3.82 (s, O—CH$_3$, 3H), 7.759-7.761 (d, 1H). $^{13}$CNMR (400 MHz, DMSO-d$_6$) δ-Value (ppm):15.80(1C), 52.13(1C), 119.21(1C), 126.37(1C), 128.38 (1C), 138.98 (1C), 160.38(1C). Mass: 237.0 [M+2], 235.0 [M].

EXAMPLE-2

Preparation of
3-bromo-4-methylthiophene-2-carboxylic acid

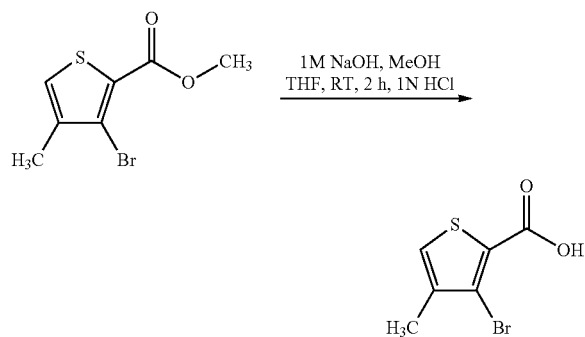

Methyl 3-bromo-4-methyl-2-thiophenecarboxylate (64.0 g, 0.272 mol) was dissolved in a mixture of methanol (288 ml) and tetrahydrofuran (288 ml), and 1N aqueous sodium hydroxide (420 ml) was added. The mixture was stirred at room temperature for 2 hrs. and acidified with 1N hydrochloric acid to give 35.5 g (59.0%) of 3-bromo-4-methyl-thiophene-2-carboxylic acid as a—off white solid, melting point 227° C. to 229° C. with 97.3% purity by HPLC.

$^1$HNMR (400 MHz, DMSO-d$_6$) δ-Value (ppm): 2.21 (d, CH$_3$, 3H), 7.692-7.794 (d, 1H), 13.30 (s, OH, 1H) $^{13}$CNMR (400 MHz, DMSO-d$_6$) δ-Value (ppm):15.98(1C), 118.45 (1C), 127.70(1C), 128.24 (1C), 138.96(1C), 161.54(1C). Mass: 221.0 [M].

EXAMPLE-3

Synthesis of
3-(cyanomethyl)-4-methy-thiophene-2-carboxylic acid

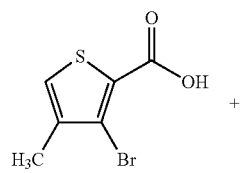
+

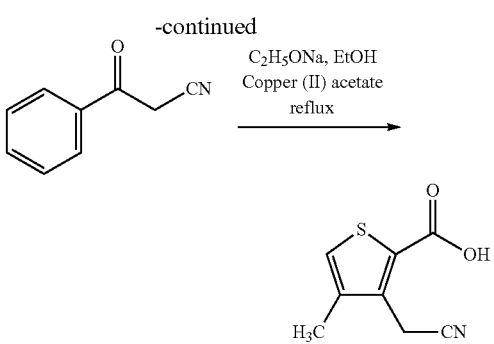

Benzoyl acetonitrile (73.8 g, 0.508 mol) was added to a cooled solution of sodium ethoxide (prepared by dissolving 19.5 g of sodium metal 0.847 mol in ethanol 1125 ml). 3-bromo-4-methyl-thiophene-2-carboxylic acid (75.0 g, 0.339 mol) was added and the mixture was stirred at room temperature for 2 hr. 4.5 g (0.0247 mol, 0.07 meq) of copper (II) acetate anhydrous was added and the mixture was boiled under reflux for 2 hours. 4.5 g (0.0247 mol, 0.07 meq) of copper (II) acetate anhydrous was added and the mixture was boiled under reflux for 8 hr. The mixture was cooled to room temperature and filtered the mass. Ethanol was removed by distillation under vacuum at a temperature 60° C. The reaction mixture was diluted with 750 ml of water while maintaining at 25-30° C. by cooling and the solution was acidified with hydrochloric acid, and extracted with two 750 ml portions of ethyl acetate. The ethyl acetate extracts were combined, and extracted with two times with 750 ml portions of 5% sodium carbonate solution. The aqueous sodium carbonate extracts were combined, the solution was acidified with hydrochloric acid, and extracted with two 325-ml portions of ethyl acetate. The ethyl acetate was removed by distillation under vacuum, to give a crude product and recrystallization of crude product from isopropyl ether to give 35.10g (57.14%) of yellow solid, melting point 140° C. to 143° C. with 94.1% purity by HPLC.

$^1$HNMR (400 MHz, DMSO-d$_6$) δ-Value (ppm): 2.24 (s, CH$_3$, 3H), 4.25 (s, CH$_2$, 2H), 7.58 (d, 1H), 13.65 (s, OH, 1H). $^{13}$CNMR (400 MHz, DMSO-d$_6$) δ-Value (ppm):14.05 (1C), 117.46 (1C), 128.10(1C), 130.18 (2C), 135.58 (1C), 138.55 (1C), 163.02 (1C). Mass: 180.1 [M-1]

EXAMPLE-4

Preparation of 5, 7-dibromo-3-methylthieno [2, 3-c] pyridine

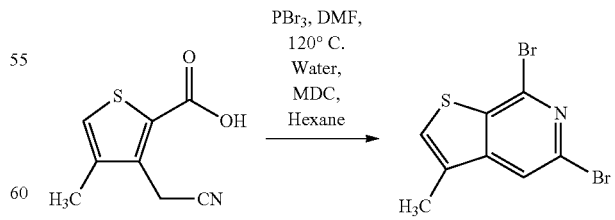

3-(cyanomethyl)-4-methyl-2-thiophenecarboxylic acid (56.0 g, 0.309 mol) was reacted in phosphorous tribromide (371 ml) and dimethylformamide (35 ml) at 120-125° C., for 4 hr. The reaction mixture was cooled to room temperature. Under cooling reaction mixture to was added to the ice water (3920 ml) to give solid crude product. The crude product was dissolved in methylene chloride (560 ml), and washed with 560 ml of water, and dried over anhydrous sodium sulfate. The methylene chloride was removed by distillation under vacuum and solid was triturated with hexane to give 67.7 g (71.2%) as a light brown solid, melting point 148° C. to 150° C., with 94.3% purity by HPLC.

¹HNMR (400 MHz, DMSO-d6) δ-Value (ppm):2.41(d, 3H), 7.41 (d, 1H), 7.76 (s, 1H) ¹³CNMR (400 MHz, CDCl3) δ-Value (ppm):13.78 (1C), 119.46(1C), 130.03 (1C), 132.37 (1C), 133.31(1C), 134.06 (1C), 138.68 (1C), 148.18 (1C). Mass: 308.12[M+1].

EXAMPLE-5

Preparation of 4-(5-bromo-3-methylthieno-[2, 3-c] pyridine-7-yl)-morpholine

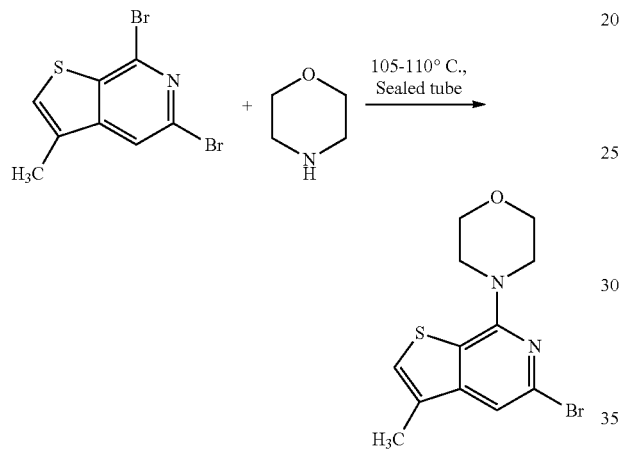

A solution of 100 g (0.325 mol) of 5, 7-dibromo-3-methylthieno [2, 3-c] pyridine dissolved in 275 ml of ethanol and 284.4 g (3.271 mol) of morpholine was heated in a sealed tube, constant-temperature at 105-110° C. for 4 hr. The ethanol and excess morpholine were removed by distillation under vacuum, the crude product was dissolved in methylene chloride (2000 ml), and washed with four 600 ml portions of water, and dried over anhydrous sodium sulfate. The methylene chloride was removed by distillation under vacuum and solid was triturated with di isopropyl ether to give 61.17 g (60.0%) of light brown solid, with 97.4% purity by HPLC.

¹HNMR (400 MHz, DMSO-d6) δ-Value (ppm): 2.36 (d, CH₃, 3H), 3.71-3.73 (t, 4H, 2 CH₂), 3.86-3.88 (t, 4H, 2 CH₂), 7.19-7.20 (d, 1H), 7.27 (s, 1H). ¹³CNMR (400 MHz, CDCl₃) δ-Value (ppm): 13.65 (1C), 48.08 (2C), 66.82 (2C), 112.11 (2C), 122.07(1C), 126.13(1C), 130.78 (1C), 133.93 (1C), 149.74 (1C), 154.95 (1C). Mass: 313.21 [M]

EXAMPLE-6

Preparation of 1-methane sulfonylpiperazine

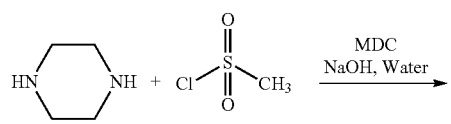

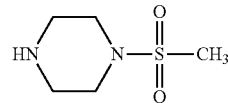

To a stirred solution of 100.0 g (1.16 mol) of piperazine dissolved in 2000 ml of methylene chloride, was added drop wise of 133.2 g (1.16 mol) of methanesulfonyl chloride at 25-30° C. . When addition was complete, the reaction mixture was stirred for 16 hrs. and mass was basified with 25% w/v aqueous sodium hydroxide. The reaction mass was filtered and washed with 800 ml of water, and dried over anhydrous sodium sulfate. The methylene chloride was removed by distillation under vacuum to give 81.2 g (42.5%) as an off white solid with 98.3% purity by chemical assay.

¹HNMR (400 MHz, DMSO-d6) δ-Value (ppm): 1.64 (s, NH, 1H), 2.77 (s, CH₃, 3H), 2.95-2.98 (t, 4H, 2 CH₂), 3.18-3.21 (t, 4H, 2 CH2). ¹³CNMR (400 MHz, CDCl3) δ-Value (ppm): 33.85 (1C), 45.34 (2C), 46.54 (2C). Mass: 165.1 [M+1]

EXAMPLE-7

Preparation of 5-bromo-3-methyl-7-mornholino-thieno [2, 3-c] pyridine

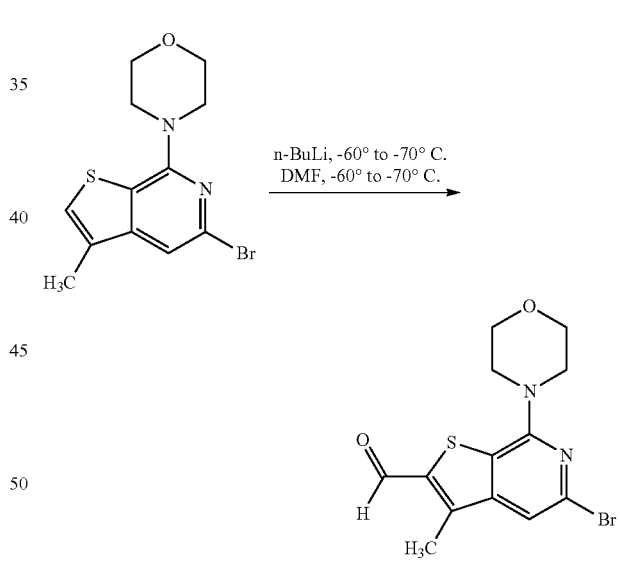

To a stirred solution of 50 g (0.1597 mol) of 4-(5-bromo-3-methylthieno-[2, 3-c] pyridine-7-yl)-morpholine in a dry tetrahydrofuran (750 ml) at −60° to −70° C. was added a 120 ml (0.192 mol) of 1.6 M n-butyl lithium in hexane. After stirring for 1 ½ hrs, 29.0 g (0.39 mol) of dry dimethyl formamide was added. The reaction mixture was stirred for 1 hr. at −60° to −70° C. and then warmed slowly to room temperature. After a further 2 hrs maintenance at room temperature the reaction mixture was poured into ice/water (2250 ml) and extracted with two 1000 ml portions of ethyl acetate. The ethyl acetate extracts were combined, and dried over anhydrous sodium sulfate. The ethyl acetate was removed by distillation under vacuum at 60° C. to give 35.30 g (64.7%) as a yellow solid, melting point 170° C. to 182.5° C. with 96.4% purity by HPLC.

¹HNMR (400 MHz, CDCl3) δ-Value (ppm): 2.41(s, 3H, CH₃), 3.63 (t, 4H, 2 CH₂), 3.73 (t, 4H, 2CH₂), 8.16 (s, 1H), 10.34 (s, 1H). ¹³CNMR (400 MHz, CDCl₃) δ-Value (ppm): 11.9 (1C), 48.7 (2C), 66.6 (2C), 112.4 (1C), 123.2(1C), 132.4(1C), 134.5(1C), 147.3(1C), 150.0 (1C), 155.1(1C), 183.8 (1C, C=O). Mass: 340.9 [M].

EXAMPLE-8

Preparation of 4[5-bromo-3-methyl-2-[(4-methylsulfonylpiperazin-1-yl) methyl] thieno [2, 3-c] pyridin-7-yl] morpholine

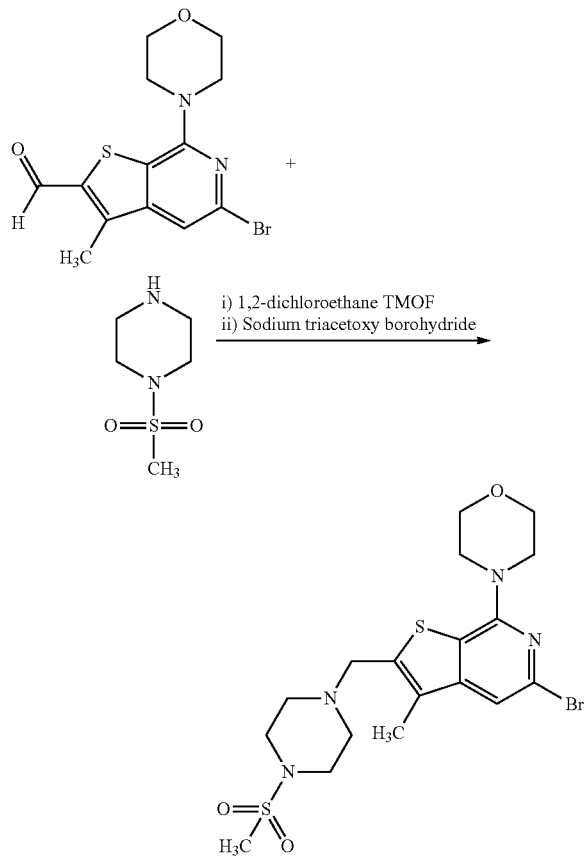

To a stirred solution of 107.0 g (0.3137 mol) of 5-bromo-3-methyl-7-morpholino-thieno [2, 3-c] pyridine, 82.0 g (0.50 mol) of 1-methane sulfonylpiperazine, and 700 g of trimethyl orthoformate in 3210 ml of 1,2-dichloroethane for 4 hours. 700 g of trimethyl orthoformate was added and the reaction mixture was stirred for 16 hrs. at room temperature. To this was added 205.5 g (0.9693 mol) of sodium triacetoxy borohydride and 1070 ml of 1, 2-dichloroethane. The reaction mixture was stirred for 4 hrs at room temperature. The mixture was then quenched with 5350 ml of water, extracted with extracted with two 1750-ml portions of methylene chloride. The methylene chloride extracts were combined, and dried over anhydrous sodium sulfate. The solvents were removed by distillation under vacuum to give the crude product. The crude solid product was twice recrystallized from acetonitrile (640 ml) to give 84.2 g (54.87%) as a brown solid, melting point 212° C. to 215° C. with 94.7% purity by HPLC.

¹HNMR (400 MHz, CDCl3) δ-Value (ppm): 2.27(s, 3H, CH₃), 2.64 (t, 4H, 2 CH₂), 2.8 (s, 3H, CH³), 3.27 (t, 4H, 2 CH₂), 3.67 (t, 4H, 2 CH₂), 3.79 (s, 2H, 1CH₂), 3.85 (t, 4H, 2 CH₂), 7.20(s, 1H). ¹³CNMR (400 MHz, CDCl3) δ-Value ppm) 11.7(1C), 34.4(1C), 45.7(2C), 48.1(2C), 52.5(2C), 54.9 (2C), 66.8(1C), 112.0(1C), 120.7(1C), 128.5(1C), 134.0 (1C), 141.3 (1C), 150.9 (1C), 154.6(1C). Mass: 491.1 [M+2], 489.1[M]

EXAMPLE-9

Preparation of 5-[3-methyl-2-[(4-methylsulfonylpiperazin-1-yl) methyl]-7-morpholino-thieno [2, 3-c] pyridin-5-yl] pyrimidin-2-amine (Compound-1).

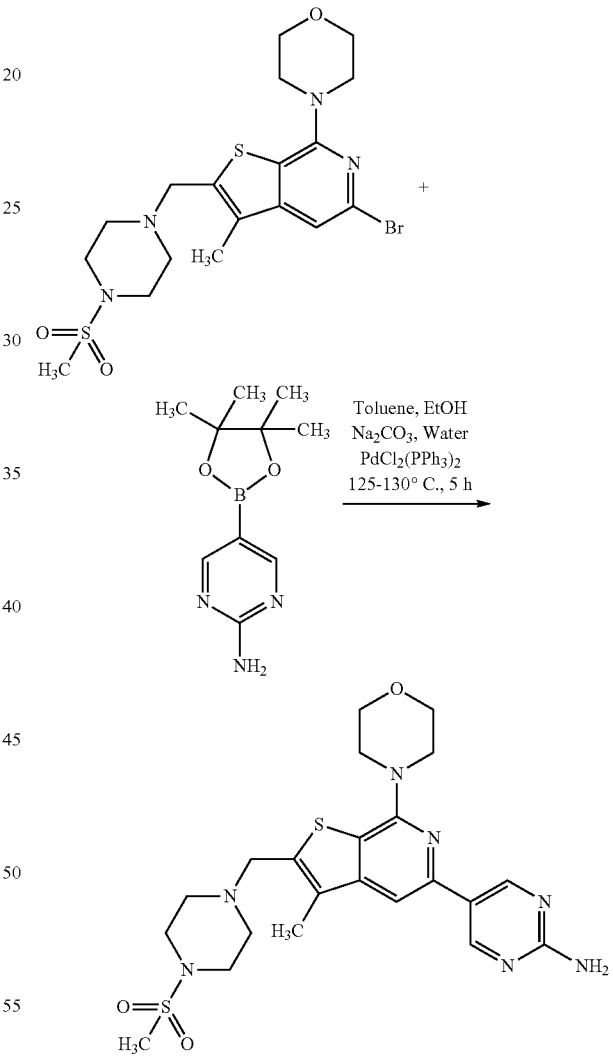

A mixture of 44.0 g (0.0899 mol) of 4-[5-bromo-3-methyl-2-[(4-methylsulfonylpiperazin-1-yl) methyl] thieno [2, 3-c] pyridin-7-yl] morpholine, 21.80 g (0.0986 mol, 1.10 meq) 2-aminopyrimidine-5-boronic acid pinacol ester, 4.0 g (0.0056 mol, 0.06 meq) bis (triphenylphosphine) palladium (II) dichloride, ethanol (300 ml), toluene (300ml), water (100 ml) and 33.30 g (0.3146 mol, 3.50 meq) of sodium carbonate was heated to 125-130° C. in the sealed the glass tube for 5 hr. The reaction mixture was cooled and the solvents were removed by distillation under vacuum to give the crude product. The crude solid product was purified by acid-base purification method to give 35.10 g (77.65%) as a-light brown solid with HPLC purity 99.7%.

¹HNMR (400 MHz, CDCl3) δ-Value (ppm): 2.36(s,3H, CH₃),2.58 (t, 4H, 2-CH₂), 2.89(s, 3H), 3.13(t, 4H, 2-CH₂), 3.59 (t, 4H, 2-CH₂), 3.79 (t, 4H,2-CH₂), 3.83 (s, 2H,CH₂), 5.24(s,2H,NH₂), 7.70 (s,1H), 9.00 (s,2H). ¹³CNMR (400 MHz, CDCl3) δ-Value ppm): 11.5(1C), 33.7(1C), 45.3 (2C), 47.9 (2C), 51.8 (2C), 53.9 (2C), 66.1(1C), 103.6 (1C), 119.6 (1C), 121.4 (1C), 129.1(1C), 140.7 (1C), 145.4 (1C), 149.5 (1C), 154.4 (1C), 156.1(2C), 163.2(1C). Mass: 504.1[M+1]

EXAMPLE-10

Preparation of 5[3-methyl-2-[(4-methylsulfonylpiperazin-1-yl) methyl]-7-morpholino-thieno [2, 3-c] pyridin-5-yl] pyrimidin-2-amine dihydrochloride (Compound-1.2HCl).

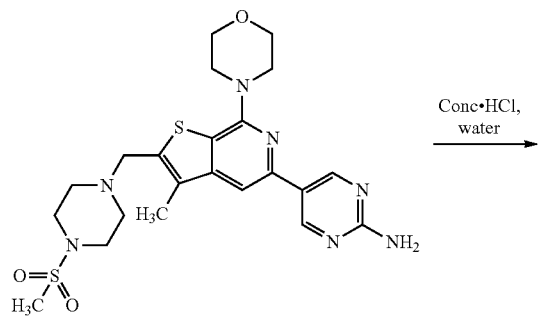

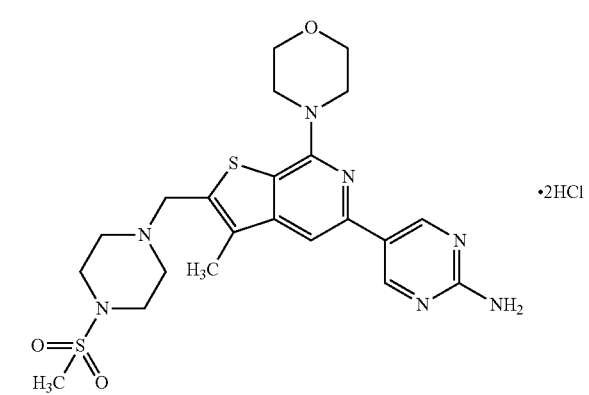

To a stirred solution of 15.0 g of 5-[3-methyl-2-[(4-methylsulfonylpiperazin-1-yl) methyl]-7-morpholino-thieno [2, 3-c] pyridin-5-yl] pyrimidin-2-amine in 75.0 ml of concentrated hydrochloric acid was added 600 ml of water. The reaction mixture was stirred for 2 hr at room temperature during which time as a yellow precipitate gradually crushed out. The solid was filtered and washed with 1N hydrochloric acid, dried under vacuum at 80-85° C. to give 15.10 g (88.0%) as a—yellow solid with HPLC purity 99.4% and dihydrochloride content 99.13% by theory.

EXAMPLE-11

Preparation of 5[3-methyl-2-[(4-methylsulfonylpiperazin-1-yl) methyl]-7-morpholino-thieno [2, 3-c] pyridin-5-yl] pyrimidin-2-amine ditosylate (Compound-1. di-tosylate)

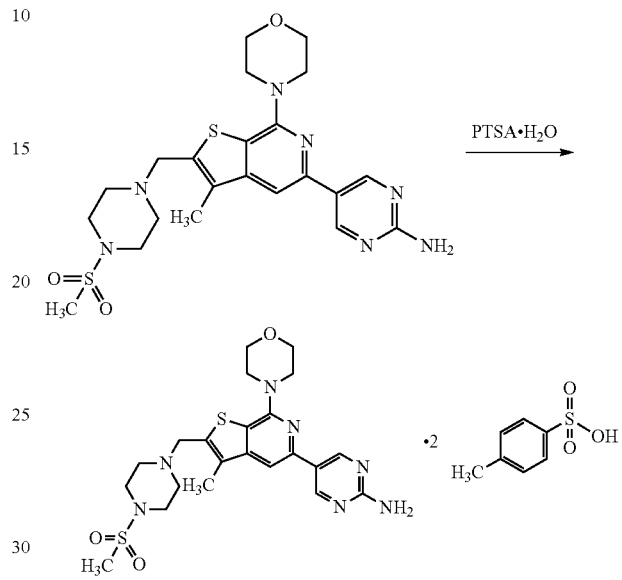

To a stirred solution of 10.0 g (0.01985 mol) of 5-[3-methyl-2-[(4-methylsulfonylpiperazin-1-yl) methyl]-7-morpholino-thieno [2, 3-c] pyridin-5-yl] pyrimidin-2-amine in a methylene chloride (500 ml) and methanol (100 ml) was added a p-toluene sulfonic acid monohydrate (8.30 g, 0.04367 mol, 2.20 meq). Then solvents were removed by distillation under vacuum to give as a yellow solid. Then the solid was triturated with 300 ml of acetone, dried under vacuum at 40-45° C. to give 15.10 g (89.97%) as a yellow solid with HPLC purity 99.7% and ditosylate content was 100.5% w/w by theory.

EXAMPLE-12

Preparation of 5[3-methyl-2-[(4-methylsulfonylpiperazin-1-yl) methyl]-7-morpholino-thieno [2, 3-c] pyridin-5-yl] pyrimidin-2-amine dimesylate (Compound-1. dimesylate)

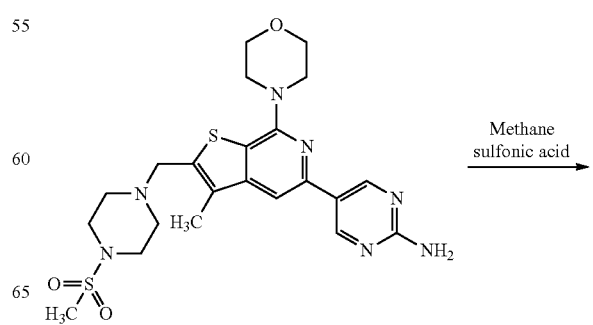

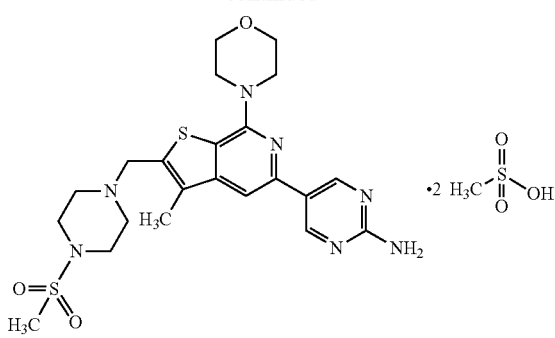

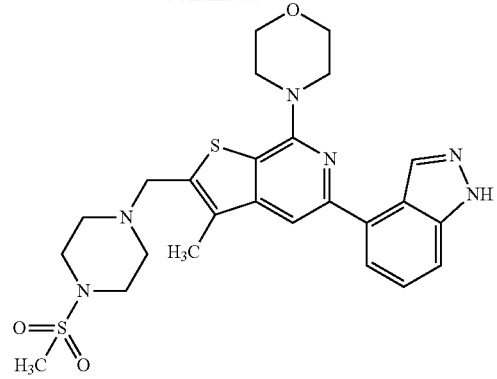

To a stirred solution of 12.0 g (0.02382 mol) of 5-[3-methyl-2-[(4-methylsulfonylpiperazin-1-yl) methyl]-7-morpholino-thieno [2, 3-c] pyridin-5-yl] pyrimidin-2-amine in a methylene chloride (600 ml) and methanol (120 ml) was added a 9.40 g (0.0952 mol, 4.0 meq) of methane sulfonic acid. The reaction mixture was stirred for 3 hrs. at room temperature during which time as a yellow precipitate gradually crushed out. The solid was filtered and leached with acetone (180 ml), dried under vacuum at 50-55° C. to give 16.10 g (97.16%) yellow solid with HPLC purity 99.8% and dimesylate content 99.6% w/w by theory.

EXAMPLE-13

Preparation of 4 [5-(1H-indazol-4-yl)-3-methyl-2-[(4-methylsulfonylpiperazin-1-yl) methyl] thieno [2, 3-c] pyridin-7-yl] morpholine (Compound-6)

A mixture of 200 mg (0.40 mmol) of 4-[5-bromo-3-methyl-2-[(4-methylsulfonylpiperazin-1-yl) methyl] thieno [2, 3-c] pyridin-7-yl] morpholine, 200 mg (0.80 mmol, 2.0meq) of 4-(4, 4, 5, 5-Tetramethyl-[1, 3, 2] dioxoborolan-2-yl)-1H-indazole, 50.0 mg (0.07 mmol, 0.17 meq) bis (triphenylphosphine) palladium (II) dichloride, ethanol (4 ml), toluene 4 ml), water (1 ml), 200 mg of sodium carbonate was heated to 115-120° C. in a sealed glass tube for 3 hr. The reaction mixture was cooled and the solvents were removed by distillation under vacuum to give crude product. The crude product was purified by column chromatography by using hexane and ethyl acetate to give 120 mg (55.8%) as a light brown solid.

$^1$HNMR (400 MHz, CDCl3) δ-Value (ppm):2.37(s,3H, CH$_3$),2.59(t, 4H, 2-CH$_2$), 2.90(s, 3H), 3.15(t, 4H, 2-CH$_2$), 3.64(t, 4H, 2-CH$_2$),3.84(t, 4H, 2-CH$_2$),3.92(2H,CH$_2$),7.45 (s,1H),7.94(s,1H), 7.56(d,1H),7.58(d,1H),7.69(d,1H), 13.1 (s,1H). Mass: 527.2[M+1]

EXAMPLE-14

Preparation of [3-[3-methyl-2-[(4-methylsulfonylpiperazin-1-yl) methyl]-7-morpholino-thieno [2, 3-c] pyridin-5-yl] phenyl] methanol (Compound- 7)

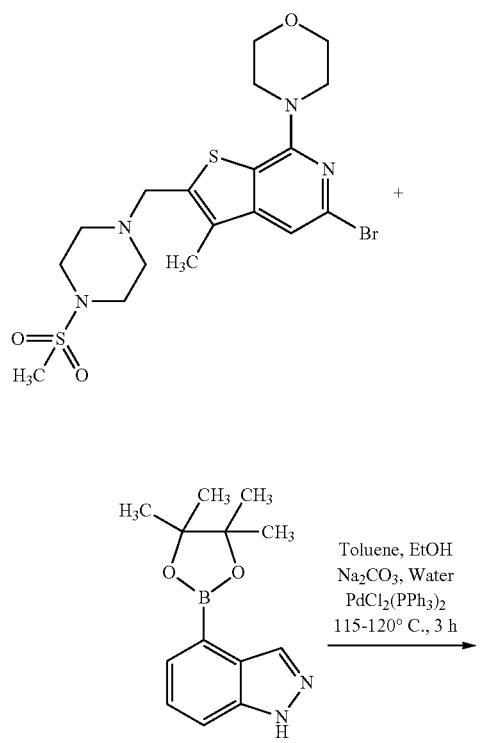

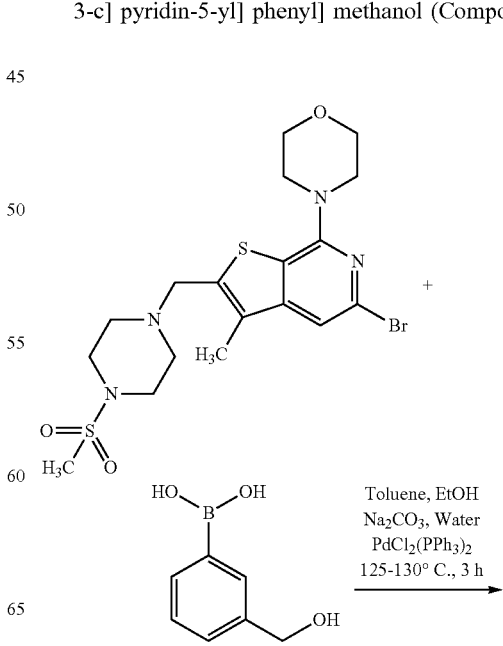

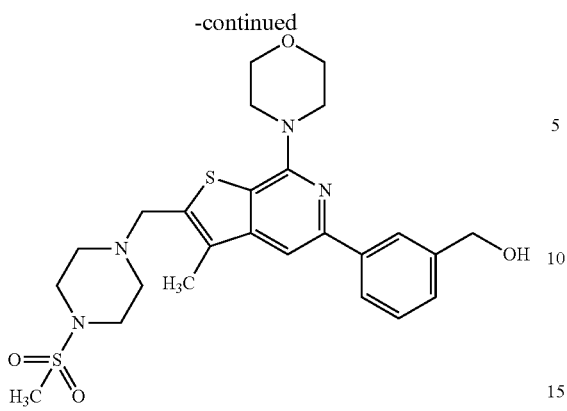

A mixture of 200 mg (0.40 mmol) of 4-[5-bromo-3-methyl-2-[(4-methylsulfonylpiperazin-1-yl) methyl] thieno [2, 3-c] pyridin-7-yl] morpholine, 124 mg (0.8 mmol, 2.0 meq) of 3-(hydroxymethyl) phenylboronic acid, 50.0 mg (0.142 mmol, 0.17 meq) bis(triphenylphosphine) palladium (II) dichloride, ethanol (4 ml), toluene 4 ml), water (1 ml) and 200 mg of sodium carbonate was heated to 115-120° C. in the sealed the glass tube for 3 hr. The reaction mixture was cooled and the solvents were removed by distillation under vacuum to give the crude product. The crude solid product was purified by column chromatography by using hexane and ethyl acetate to give 95 mg (45.2%) yellow solid.

$^1$HNMR (400 MHz, DMSO) δ-Value (ppm): 2.40(s,3H, CH$_3$),2.59(t, 4H,2-CH$_2$), 2.90(s, 3H,CH$_3$), 3.14(t, 4H, 2-CH$_2$),3.60(t, 4H, 2-CH$_2$),3.82(t, 4H, 2-CH$_2$),3.85(s,2H, CH$_2$), 4.58(d,2H),5.24(t,1H,), 7.33(d,1H),7.41(t,1H), 7.76 (s,1H),8.0(d,1H), 8.10(s,1H). $^{13}$CNMR (400 MHz, CDCl$_3$) δ-Value ppm):11.7(1C), 33.9(1C), 45.4(2C), 48.2(2C), 51.9 (2C), 54.0(1C), 63.0(1C), 66.2(2C), 105.7(1C), 120.6 (1C), 124.6(1C), 125.0(1C),126.6(1C), 128.4(1C), 129.5(1C), 139.2 (1C), 140.9(1C),142.7(1C),149.0(1C),149.6(1C), 154.5(1C). Mass: 517.3[M+1]

EXAMPLE-15

Preparation of methyl 3-bromo-2-thiophenecarboxylate

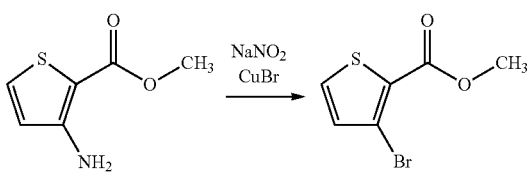

3-amino-2-thiophenecarboxylic acid methyl ester (100 g, 0.6369 mol) was suspended in hydrobromic acid (220 ml), and the mixture was stirred at room temperature for 15 min. The mixture was cooled to 0-5° C., and sodium nitrite (46.0 g, 0.666 mol) in water (100 ml) was added dropwise below 5° C. The mixture was stirred for 1 hr, and then was added to a copper (I) bromide (96.0 g, 0.6692 mol) in hydrobromic acid (260 ml) at room temperature. The resulting mixture was stirred at 60-65° C. for 2 hrs. The reaction mixture was diluted with 1200 ml of water while maintaining at 25-30° C. by cooling and extracted with two 600 ml portions of ethyl acetate. The ethyl acetate extracts were combined, washed two times with 600 ml portions of water, and dried over anhydrous sodium sulfate. The ethyl acetate was removed by distillation under vacuum at 60° C. to give 129.0 g (91.6%) as a yellow solid, melting point 47° C. to 48° C., with 96% purity by HPLC.

$^1$HNMR (400 MHz, CDCl$_3$) δ-Value (ppm): 3.90(s, O—CH$_3$, 3H), 7.09 (d, 1H), 7.46 (d, 1H).
$^{13}$CNMR (400 MHz, CDCl$_3$) δ-Value (ppm): 52.10(1C ), 116.96(1C), 127.12(1C), 130.61 (1C), 133.63 (1C), 161.0 (1C). Mass: 222.8 [M+1].

EXAMPLE-16

Preparation of 3-promo-2-thionhene carboxylic acid

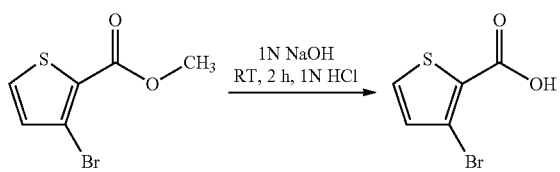

Methyl 3-bromo-2-thiophenecarboxylate 128.0 g (0.5791 mol) was dissolved in a mixture of methanol (576 ml) and tetrahydrofuran (576 ml) and 1N aqueous sodium hydroxide (876 ml) was added. The mixture was stirred at room temperature for 2 hr and acidified with 1N hydrochloric acid, and extracted with two 740 ml portions of ethyl acetate. The ethyl acetate extracts were combined, washed with 740 ml of water and dried over anhydrous sodium sulfate. The obtained product was an off-white solid, melting point 192° C. to 198.5° C., with 98.1% purity by HPLC.

$^1$HNMR (400 MHz, DMSO-d$_6$) δ-Value (ppm): 7.25-7.26 (d, 1H), 7.91-7.93 (d, 1H), 13.43 (s, OH, 1H). $^{13}$CNMR (400 MHz, DMSO-d$_6$) δ-Value (ppm): 116.02(1C), 128.35(1C), 133.19(2C), 161.66 (1C). Mass: 207 [M].

EXAMPLE-17

Preparation of 3-cyanomethyl-2-thiophenecarboxylic acid

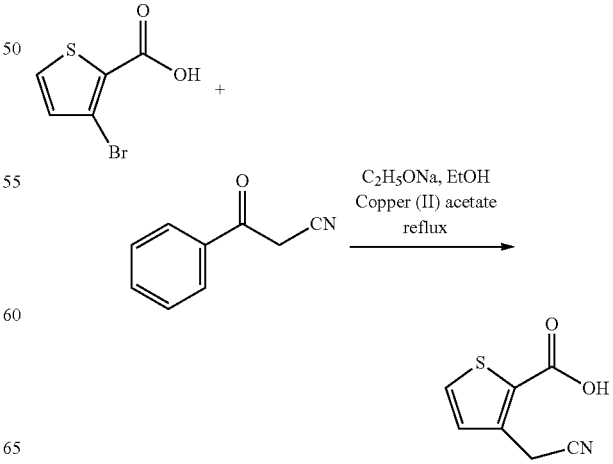

Benzoyl acetonitrile (73.8 g, 0.508 mol) was added to a cooled solution of sodium ethoxide (prepared from sodium 19.5 g, 0.847 mol. and ethanol, 1125 ml). 3-Bromo-2-thiophene-2-carboxylic acid (75.0 g, 0.362 mol) was added and the mixture was stirred at room temperature for 2 hr. 4.5 g (0.0247 mol) Of copper (II) acetate anhydrous was added and the mixture was boiled under reflux for 2 hours. 4.5 g (0.0247 mol) of copper (II) acetate anhydrous was added and the mixture was boiled under reflux for 8 hr. Mixture was cooled to room temperature and filtered the mass. Ethanol was removed by distillation under vacuum at a temperature 60° C. The reaction mixture was diluted with 750 ml of water while maintaining at 25-30° C. by cooling and the solution was acidified with hydrochloric acid, and extracted with two 750 ml portions of ethyl acetate. The ethyl acetate extracts were combined and extracted with two times with 750 ml portions of 5% sodium carbonate solution. The aqueous sodium carbonate extracts were combined, the solution was acidified with hydrochloric acid and extracted with two 325 ml portions of ethyl acetate. The ethyl acetate was removed by distillation under vacuum, to give a crude product and recrystallization of a crude product from iso-propyl ether to give 34.8 g (56.65%) as a-yellow solid, melting point 102° C. to 106° C., with 97.1% purity by HPLC.

$^1$HNMR (400 MHz, DMSO-d$_6$) δ-Value (ppm): 4.25 [s, CH$_2$ (2H)], 7.24 (d, 1H), 7.88(d, 1H), 13.44[s, (broad), OH, 1H]. $^{13}$CNMR (400 MHz, DMSO-d$_6$) δ-Value (ppm):17.72 (1C), 118.5 (1, C), 129.5(1C), 130.6 (1C), 132.46(1C), 137.0 (1C), 162.9 (1C). Mass: 167.0 [M], 166.0 [M-1]

EXAMPLE-18

Preparation of 5, 7-dibromothieno [2, 3-c] pyridine

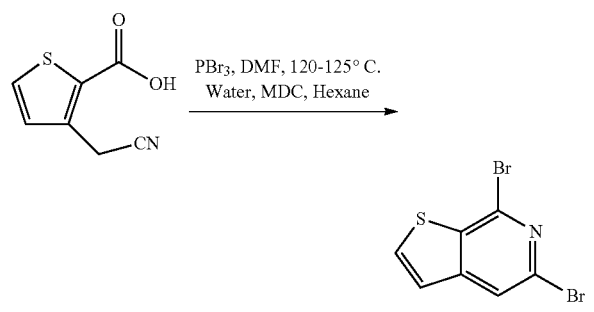

3-(Cyanomethyl)-2-thiophenecarboxylic acid (56.0 g, 0.335 mol) was reacted in phosphorous tribromide (371 ml) and dimethylformamide (35 ml) at 120-125° C. for 4 hr. The reaction mixture was cooled to room temperature. Under cooling reaction mixture was added to the ice water (3920 ml) to give solid crude product. The crude product was dissolved in methylene chloride (560 ml), washed with 560 ml of water and dried over anhydrous sodium sulfate. The methylene chloride was removed by distillation under vacuum and solid was triturated with hexane (400 ml) to give 67.7 g (71.2%) as a light brown solid, melting point 114° C. to 126.8° C.

$^1$HNMR (400 MHz, CDCl$_3$) δ-Value (ppm): 7.42 (d, 1H), 7.80(d, 1H), 7.87(s, 1H) $^{13}$CNMR (400 MHz, CDCl$_3$) δ-Value (ppm): 121.0(1C), 123.31(1C), 133.49(1C), 133.9 (1C), 134.9(1C), 138.4(1C), 147.8 (1C). Mass: 295.9 [M+2], 293.9 [M]

EXAMPLE-19

Preparation of 4-(5-bromothieno [2, 3-c] pyridin-7-yl) morpholine

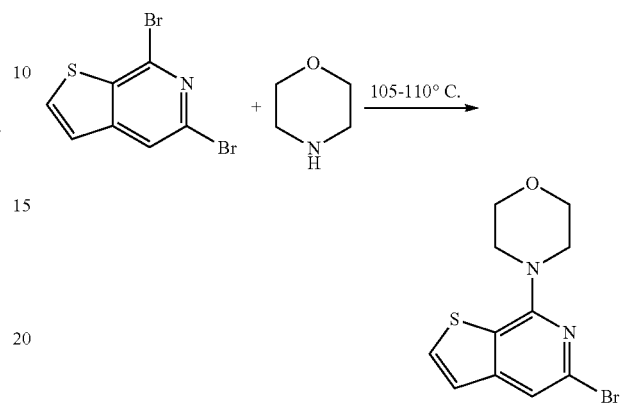

A solution of 50 g (0.1706 mol) of 5, 7-dibromothieno [2, 3-c] pyridine dissolved in 230 ml of ethanol and 230 g of morpholine was heated in a sealed tube under constant temperature at 105-110° C. for 4 hrs. The ethanol and excess morpholine were removed by distillation under vacuum, the crude product was dissolved in methylene chloride (1200 ml), washed with four 400-ml portions of water and dried over anhydrous sodium sulfate. The methylene chloride was removed by distillation under vacuum to give 45.7 g (89.5%) as a light brown solid.

$^1$HNMR (400 MHz, CDCl$_3$) δ-Value (ppm): 3.62 (t, 4H, 2 CH$_2$), 3.76 (t, 4H, 2 CH$_2$), 7.43 (d, 1H), 7.37(s, 1H) 8.05 (d, 1H). $^{13}$CNMR (400 MHz, CDCl$_3$) δ-Value (ppm): 47.50 (2C), 65.90 (2C), 113.0 (1C), 120.89 (1C), 123.19 (1C), 132.80 (1C), 133.0 (1C), 149.7(1C), 154.2(1C).

Mass: 299.15 [M], 297.2 [M-2]

EXAMPLE-20

Preparation of 5-bromo-7-morpholino-thieno [2, 3-c] pyridine-2-carbaldehyde

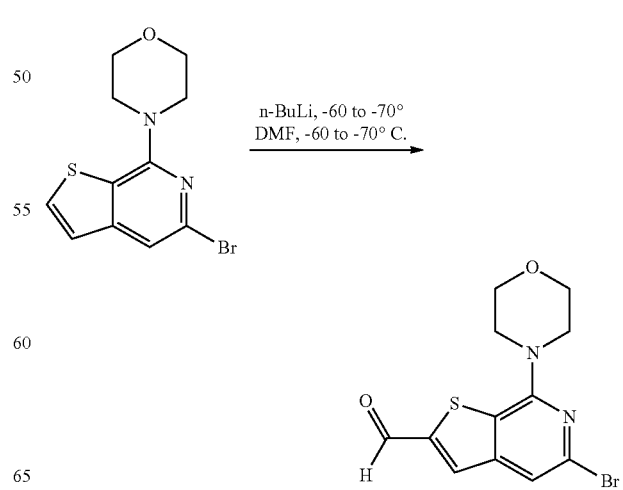

To a stirred solution of 42 g (0.1404 mol) of 4-(5-bromothieno [2, 3-c] pyridin-7-yl) morpholine in a dry tetrahydrofuran (750 ml) at −60° to −70° C. was added a 105 ml (0.168 mol) of 1.6 M n-butyl lithium in hexane. After stirring for 1 ½ hrs. 20.5g (0.28 mol) of dry dimethyl formamide was added. The reaction mixture was stirred for 1 hr. at −60° to −70° C. and then warmed slowly to room temperature. After a further 2 hrs at room temperature the reaction mixture poured into ice/water (1000 ml) and extracted with two 420 ml portions of ethyl acetate. The ethyl acetate extracts were combined and dried over anhydrous sodium sulfate. The ethyl acetate was removed by distillation under vacuum at 60° C. to give 38.40 g (83.7%) as a yellow solid, melting point 140° C. to 153.5° C., with 95.0% purity by HPLC.

$^1$HNMR (400 MHz, CDCl$_3$) δ-Value (ppm): 3.75 (t, 4H, 2 CH$_2$), 3.86 (t, 4H, 2 CH$_2$), 7.43 (s, 1H), 7.88(s, 1H), 10.13 (s, 1H). $^{13}$CNMR (400 MHz, CDCl$_3$) δ-Value (ppm): 48.0 (2C), 66.6 (2C), 114.3 (1C), 123.7(1C), 131.54(1C), 134.6 (1C), 146.2(1C), 148.2(1C), 155.0(1C), 184.3 (1C). Mass: 328.0 [M+1]

EXAMPLE-21

Preparation of 4-[5-bromo-2-[(4-methylsulfonylpiperazin-1-yl) methyl]thieno [2, 3-c] pyridin-7-yl] morpholine

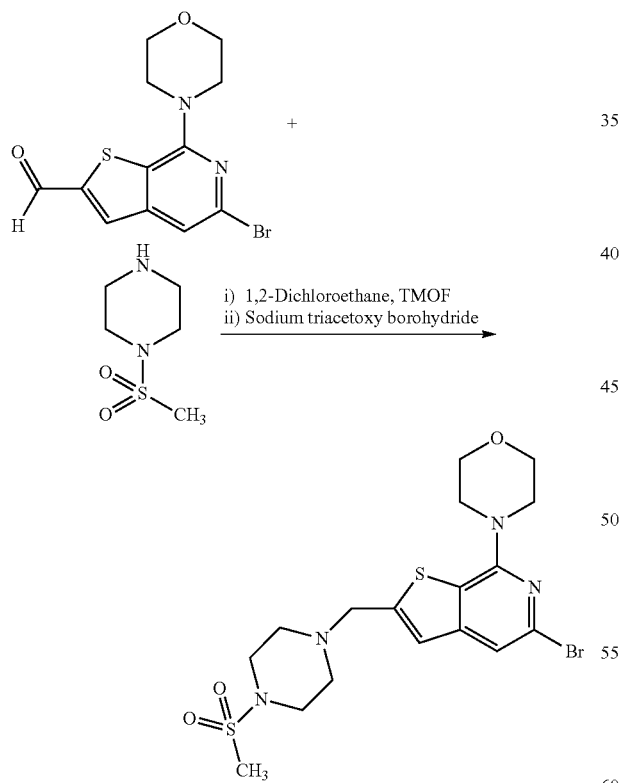

To a stirred solution of 50.0 g (0.1529 mol) of 5-bromo-7-morpholino-thieno [2, 3-c] pyridine-2-carbaldehyde, 40.0 g (0.2439 mol, 1.60 meq) of 1-methane sulfonylpiperazine, and 325 g of trimethyl orthoformate in 1500 ml of 1,2-dichloroethane for 4 hours. 325 g of trimethyl orthoformate was added and the reaction mixture was stirred for 16 hrs. at room temperature. To this was added 100 g (0.4716 mol, 3 meq) of sodium triacetoxy borohydride and 1000 ml of 1, 2-dichloroethane. The reaction mixture was stirred for 4 hrs. at room temperature. The mixture was then quenched with 2500 ml of water, extracted with two 2000 ml portions of methylene chloride. The methylene chloride extracts were combined and dried over anhydrous sodium sulfate. The solvents were removed by distillation under vacuum to give crude product. The crude solid product was twice recrystallized from acetonitrile (300 ml) to give 45.1 g (62.1%) as a brown solid, melting point 218° C. to 224° C., with 95.4% purity by HPLC.

$^1$HNMR (400 MHz, CDCl$_3$) δ-Value (ppm): 2.64 (t, 4H, 2 CH$_2$), 2.79 (s, 3H, CH$_3$), 3.27 (t, 4H, 2 CH$_2$), 3.68 (t, 4H, 2 CH$_2$), 3.83 (s, 2H, 1CH$_2$), 3.85 (t, 4H, 2 CH$_2$), 7.0 (s, 1H), 7.2(s, 1H) , Mass: 477.01[M+2]

EXAMPLE-22

Preparation of 5-[2-[(4-methylsulfonyl piperazin-1-yl)methyl]-7-morpholino-thieno[2,3-c]pyridin-5-yl] pyrimidin-2-amine (compound-2)

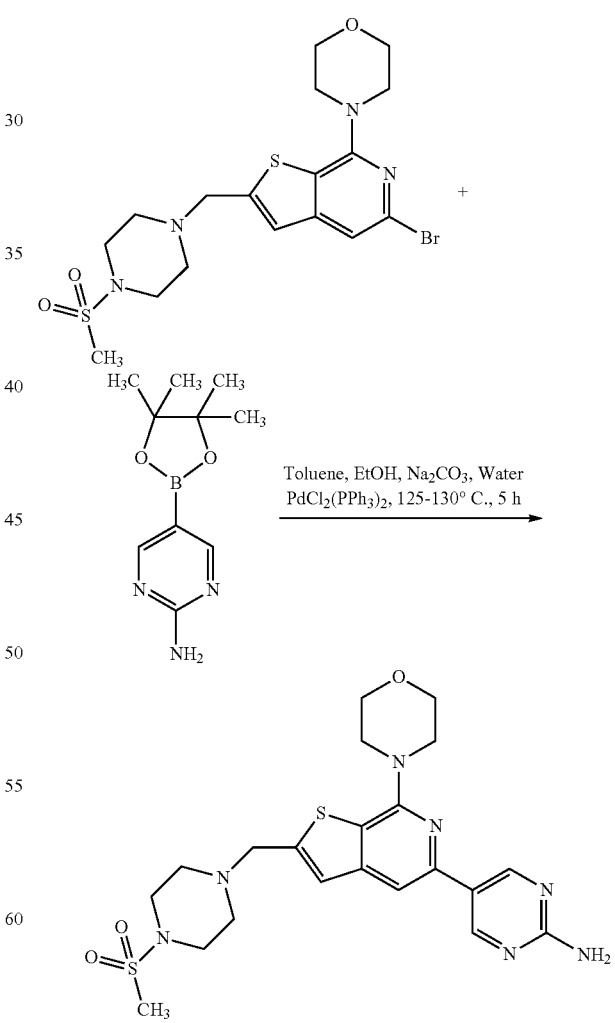

A mixture 40.0 g (0.08421 mol) of 4-[5-bromo-2-[(4-methylsulfonylpiperazin-1-yl) methyl] thieno [2, 3-c] pyridin-7-yl] morpholine, 20.4 g (0.0923 mol, 1.10 meq) of 2-aminopyrimidine-5-boronic acid pinacol ester, 3.54 g (0.0056 mol, 0.06 meq) bis (triphenylphosphine) palladium (II) dichloride, ethanol (300 ml), toluene (300ml), water (100 ml), 31.20 g of sodium carbonate (0.2943 mol, 3.50 meq) was heated to 125-130° C. in the sealed the glass tube for 5 hr. The reaction mixture was cooled and the solvents were removed by distillation under vacuum to give the crude product. The crude solid product was purified by acid-base purification method to give 33.150g (80.15%) as a light brown solid with HPLC purity 99.6%.

EXAMPLE-23

Preparation of 4-[5-(1H-indazol-4-yl)-2-[(4-methyl-sulfonylpiperazin-1-yl) methyl] thieno [2, 3-c] pyridin-7-yl] morpholine (compound-3)

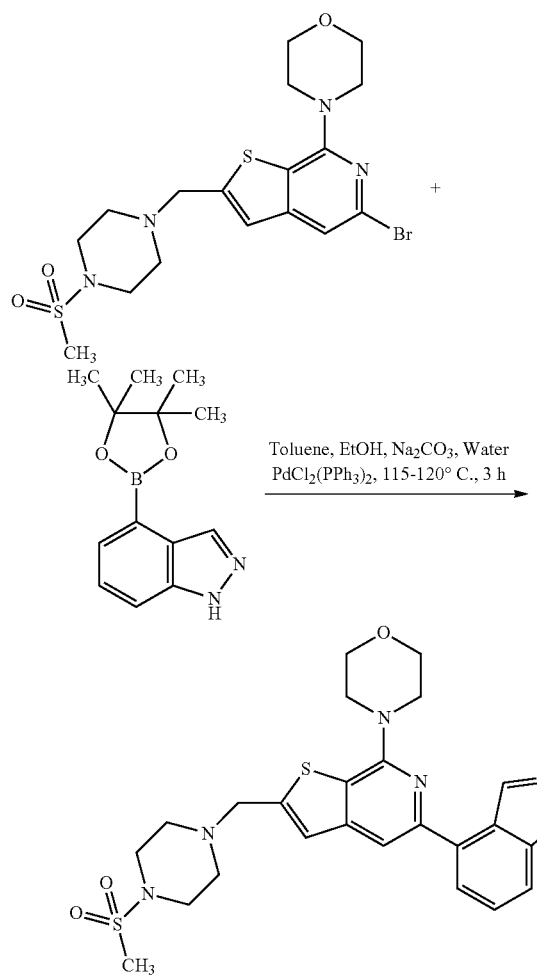

A mixture of 1.0 g (2.1 mmol) of 4-[5-bromo-2-[(4-methylsulfonylpiperazin-1-yl) methyl] thieno [2, 3-c] pyridin-7-yl] morpholine, 1.02g (4.2 mmol, 2.0meq) of 4-(4, 4, 5, 5-Tetramethyl-[1, 3, 2] dioxoborolan-2-yl)-1H-indazole, 200.0 mg (0.28 mmol, 0.13 meq) bis (triphenylphosphine) palladium (II) dichloride, ethanol (20 ml), toluene (40 ml), water (4 ml), 800 mg of sodium carbonate was heated to 115-120° C. in the sealed the glass tube for 3 hrs. The reaction mixture was cooled and the solvents were removed by distillation under vacuum to give the crude product. The crude solid product was purified by column chromatography by using hexane and ethyl acetate to give 0.8 g (74.7%) as a light brown solid.

$^1$HNMR (400 MHz, CDCl$_3$) δ-Value (ppm):2.59(t, 4H, 2-CH$_2$), 2.90(s, 3H), 3.15(t, 4H, 2-CH$_2$), 3.64(t, 4H, 2-CH$_2$), 3.84(t, 4H, 2-CH$_2$),3.92(2H,CH$_2$),7.45(s,1H),7.94(s,1H), 7.56(d,1H),7.58(d,1H),7.69(d,1H),7.43(d,IH),13.1(s,1H). Mass: 514.0[M+2], 513.0[M+1]

EXAMPLE-24

Preparation of [3-[2-[(4-methylsulfonylpiperazin-1-yl) methyl]-7-morpholino-thieno [2, 3-c] pyridin-5-yl] phenyl] methanol (compound-4)

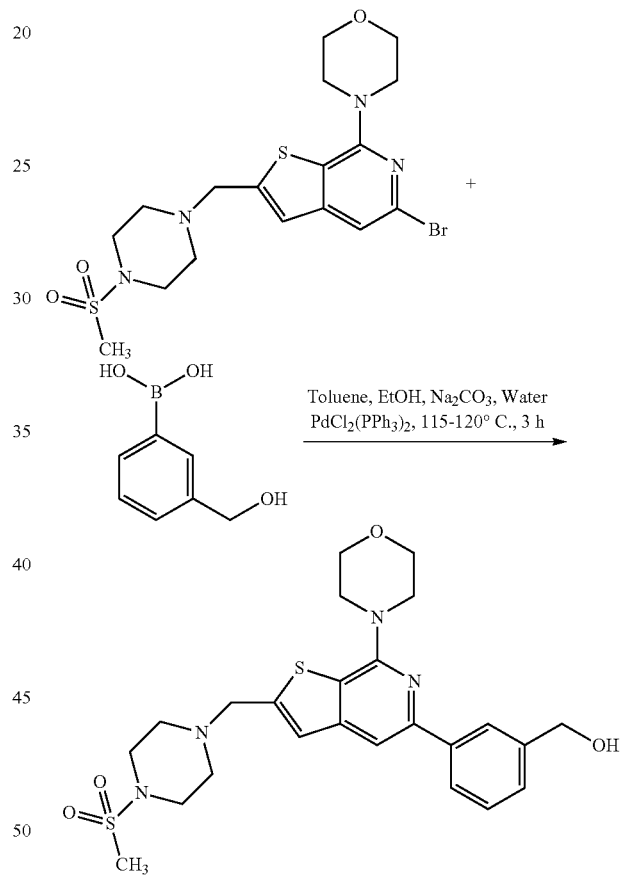

A mixture of 0.5 g (1.05 mmol) of 4-[5-bromo-2-[(4-methylsulfonylpiperazin-1-yl) methyl] thieno [2, 3]pyridin-7-yl] morpholine, 0.32g (2.10mmol, 2.0 meq) of 3-(hydroxymethyl) phenylboronic acid, 100.0 mg (0.142 mmol, 0.13 meq) bis (triphenylphosphine) palladium (II) dichloride, ethanol (20 ml), toluene 20 ml), water (2 ml), 400 mg of sodium carbonate was heated to 115-120° C. in the sealed the glass tube for 3 hr. The reaction mixture was cooled and the solvents were removed by distillation under vacuum to give the crude product. The crude solid product was purified by column chromatography by using hexane and ethyl acetate to give 450 mg (86.5%) as a yellow solid.

$^1$HNMR (400 MHz, DMSO) δ-Value (ppm): 2.57(t, 4H,2-CH$_2$), 2.89(s, 3H,CH$_3$), 3.14(t, 4H, 2-CH$_2$),3.60(t, 4H, 2-CH$_2$),3.82(t, 4H, 2-CH$_2$),3.89(s,2H, CH$_2$), 4.47(d,1H), 4.57(d,2H), 7.29(t,2H),7.42(t,2H), 7.99(s,1H),8.0(s,1H). $^{13}$CNMR (400 MHz, CDCl$_3$) δ-Value ppm):33.8 (1C), 45.4 (2C), 48.3(2C), 51.8(2C), 56.2(1C), 59.8(1C), 63.1(1C), 66.2(2C), 107.1(1C), 121.4 (1C), 122.8(1C), 124.8(1C), 126.6(1C), 127.2(1C), 132.5(1C), 139.0 (1C), 141.2(1C), 142.8(1C),147.7(1C),154.4(1C). Mass: 504.1[M+2], 503.1 [M+1]

EXAMPLE-25

Preparation of 3-[2-[(4-methylsulfonylpiperazin-1-yl) methyl]-7-morpholino-thieno [2, 3-c] pyridin-5-yl] aniline (compound-5)

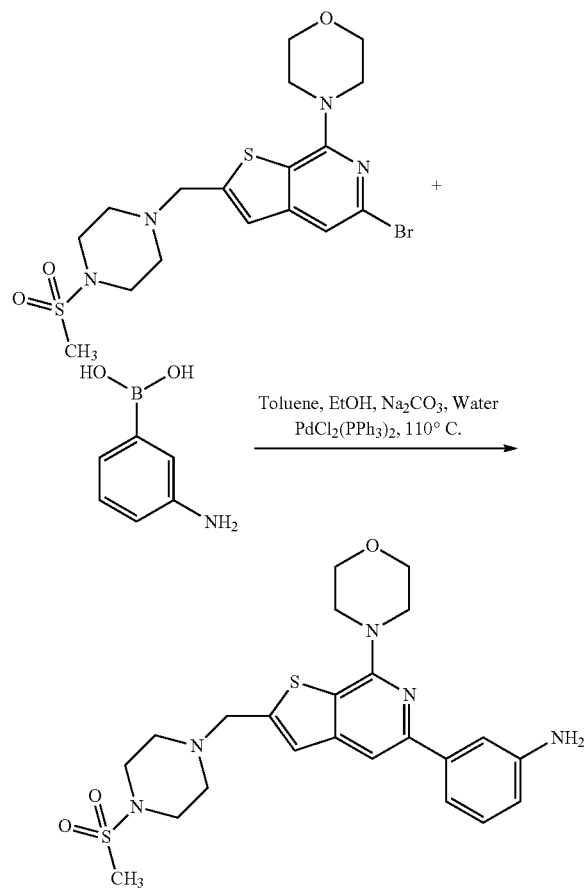

A mixture of 1.0 g (2.1 mmol) of 4-[5-bromo-2-[(4-methylsulfonylpiperazin-1-yl) methyl] thieno [2, 3-c]pyridin-7-yl] morpholine, 0.65 g (4.2 mmol, 2.0meq) of 3-aminophenylboronicacid monohydrate, 200.0 mg (0.28 mmol, 0.13 meq) bis (triphenylphosphine) palladium (II) dichloride, ethanol (20 ml), toluene (40 ml), water (4 ml), 800 mg of sodium carbonate was heated to 125-130° C. in the sealed the glass tube for 5 hr. The reaction mixture was cooled and the solvents were removed by distillation under vacuum to give the crude product. The crude solid product was purified by recrystallization using hexane and ethyl acetate to give 0.78 g (76.4%) as a light brown solid.

$^1$HNMR (400 MHz, DMSO) δ-Value (ppm): 2.57(t, 4H,2-CH$_2$), 2.89(s, 3H,CH$_3$), 3.14(t, 4H, 2-CH$_2$),3.61(t, 4H, 2-CH$_2$),3.80(t, 4H, 2-CH$_2$),3.87(s,2H, CH$_2$), 5.13(s,2H, NH$_2$),6.57(d, 1H),7.0(t,1H),7.21(d,1H), 7.38(s,1H),7.68 (1H).
$^{13}$CNMR (400 MHz, CDCl$_3$) δ-Value ppm):33.8 (1C), 45.4(2C), 48.1(2C), 51.8(2C), 56.3(1C), 66.2(2C),106.9 (1C),112.1(1C),114.2(1C),114.3(1C),121.1(1C),122.9(1C), 129.1(1C),139. 9(1C),147.5(1C),148.6(1C),148.7(1C), 149.7(1C),154.3(1C). Mass: 488.3[M+1]

EXAMPLE-26

Preparation of 3-[3-methyl-2-[(4-methyl sulfonylpiperazin-1-yl) methyl]-7-morpholino-thieno[2,3-c]pyridin-5-yl]aniline (compound 8)

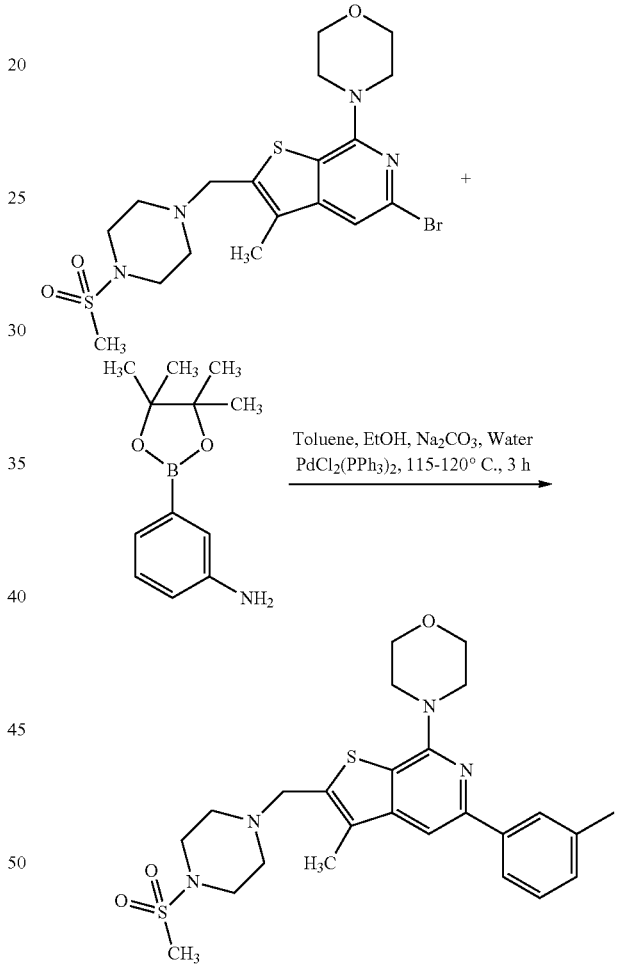

A mixture of 1.0 g (2.1 mmol) of 4-[5-bromo-3-methyl-2-[(4-methylsulfonylpiperazin-1-yl) methyl] thieno [2, 3-c] pyridin-7-yl] morpholine, 0.92 g (4.2 mmol, 2.0meq) of 3-aminophenyl boronic acid pinacol ester, 200.0 mg (0.28 mmol, 0.13 meq) bis (triphenylphosphine) palladium (II) dichloride, ethanol (20 ml), toluene (40 ml), water (4 ml), 800 mg of sodium carbonate was heated to 125-130° C. in the sealed the glass tube for 5 hrs. The reaction mixture was cooled and the solvents were removed by distillation under vacuum to give the crude product. The crude solid product was purified by using hexane and ethyl acetate to give 0.82 g (80%) as a light brown solid.

¹HNMR (400 MHz, DMSO) δ-Value (ppm): 2.57(t, 4H,2-CH₂), 2.89(s, 3H,CH₃), 3.14(t, 4H, 2-CH₂),3.60(t, 41-1, 2-CH₂),3.79(t, 4H, 2-CH₂),3.88(s,2H, CH₂), 6.87(s, 2H,NH₂),7.32(s,114),7.73(s,1H), 8.93(s,2H).
¹³CNMR (400 MHz, CDCl₃) δ-Value ppm):33.8 (1C), 45.4(2C), 48.0(2C), 51.8(2C), 56.2(1C), 66.2(2C), 105.1 (1C), 120.6(1C), 121.5(1C), 121.5(1C), 122.7(1C), 145.5 (1C), 147.8(1C), 148.6(1C), 154.5(1C), 156.2(1C), 163.2 (1C).
Mass: 491.3[M+2], 490.3[M+1]

EXAMPLE-27

Preparation of methyl 3-methylthiophene-2-carboxylate

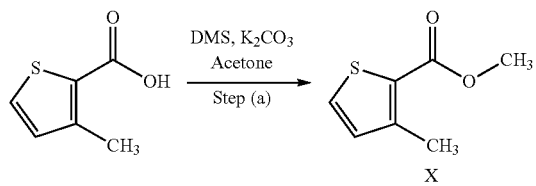

To a stirred solution of 100 g (0.7023 mol) of 3-methyl-2-thiophene carboxylic acid in 1000 ml of acetone was added 122.0 g (0.8827 mol) of potassium carbonate in 500 ml of acetone and was added drop wise of 89.0 g (0.7056 mol) of dimethyl sulfate, while maintaining the temperature of the reaction mixture at 25-30° C. When the addition was complete, the solution was stirred at 25-30° C. for 4 hr. The acetone was removed by distillation under vacuum and the reaction mixture was diluted with 3000 ml of water while maintaining at 25-30° C. by cooling and extracted with three 1000 ml portions of ethyl acetate. The ethyl acetate extracts were combined, washed two times with 1000 ml portions of water, and dried over anhydrous sodium sulfate. The ethyl acetate was removed by distillation under vacuum at 60° C. to give 105.2 g (95.6%) as a light yellow oily mass with 99.8% purity by HPLC.

EXAMPLE-28

Preparation of methyl 3-(bromomethyl) thiophene-2-carboxylate

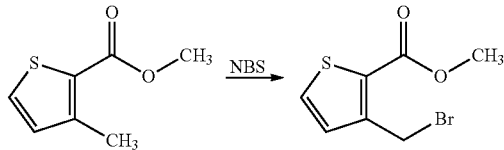

To a stirred solution of 200 g (1.2805 mol) of methyl 3-methylthiophene-2-carboxylate in 1220 ml of carbon tetrachloride was added 228.0 g (1.2805 mol) of N-bromosuccinimide and 12.40 g (0.0512 mol) of benzoyl peroxide was added while maintaining the temperature of the reaction mixture at 25-30° C. When the addition was complete, the reaction mixture was heated to 75-80° C. and was stirred for 4 hr. The reaction mixture was filtered and washed with 100 ml of carbon tetrachloride. The filtrate mass was withed two1660-ml portions of 5% sodium carbonate and two times with 1660-ml portions of water, and dried over anhydrous sodium sulfate. The carbon tetrachloride was removed by distillation under vacuum at 65° C. to give crude product. Then crude product was triturated with hexane (540 ml) to give 190.0 g (63.0%) as a—solid with 97.4% purity by HPLC.

EXAMPLE-29

Preparation of 3-cyanomethyl -2-thiophene-2-carboxylate

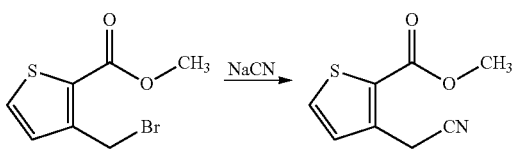

To a stirred solution of 51.50 g (1.05 mol) of sodium cyanide in 220 ml of water was added 185,0 g (0.7868 mol) of 3-(bromomethyl) thiophene-2-carboxylate and 500 ml of methanol. When the addition was complete, the reaction mixture was heated to 50-55° C. and was stirred for 2 hr. The reaction mixture was diluted with 4800 ml of water while maintaining at 25-30° C. by cooling and extracted with two1800 ml portions of ethyl acetate. The ethyl acetate extracts were combined, washed two times with 1800 ml portions of water, and dried over anhydrous sodium sulfate. The ethyl acetate was removed by distillation under vacuum at 60° C. to give crude product. Then crude product was triturated with hexane (680 ml) to give 119.0 g (83.0%) as a light brown solid with 88.8% purity by HPLC.

EXAMPLE-30

Preparation of 3-cyanomethyl -2-thiophenecarboxylic acid

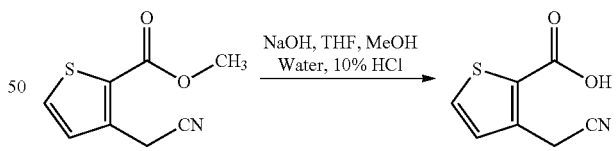

115.0 g (0.6352 mol) Of 3-cyanomethyl-2-thiophene-2-carboxylate was dissolved in a mixture of methanol (575 ml) and tetrahydrofuran (575 ml), and 1N aqueous sodium hydroxide (900 ml) was added. The mixture was stirred at room temperature for 2 hrs. and reaction mixture was diluted with 3450 ml of water and acidified with 1N hydrochlotic acid, and extracted with two 1725 ml portions of ethyl acetate. The ethyl acetate extracts were combined, washed with 3450 ml of water, and dried over anhydrous sodium sulfate. The ethyl acetate was removed by distillation under vacuum at 60° C. to give crude product. Then crude product was triturated with hexane (1150 ml) to give 95.2 g (89.7%) as an off white solid with 89.4% purity by HPLC.

EXAMPLE-31

Preparation of 5-bromo-3-methyl-7-morpholino-4-nitro-thieno[2,3-c]pyridine-2-carbaldehyde:

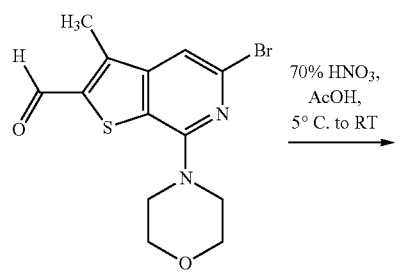

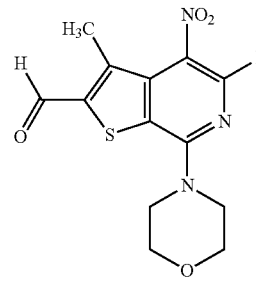

A mixture of 13 g (38 mmol) of 5-bromo-3-methyl-7-morpholino-thieno [2,3-c]pyridine-2-carbaldehyde was reacted with 11.2 mL (95 mmol, 2.3 meq) of 70% nitric acid in acetic acid (200 mL) at 5-10° C. in a 4 necked round bottomed flask for 1 h. The reaction mixture was quenched in crushed ice and filtered to afford 12.5 g of 5-bromo-3-methyl-7-morpholino-4-nitro-thieno[2,3-c] pyridine-2-carbaldehyde as yellowish green colour solid.

$^1$HNMR (400 MHz, CDCl$_3$, δ ppm): 2.58 (s, 3H, CH$_3$); 3.89 (m, 8H, 4 X CH$_2$); 10.34 (s, 1H, CHO). Mass: 388.1 [M+2]

EXAMPLE-32

Preparation of 4-[5-bromo-3-methyl-2-[(4-methylsulfonylpiperazin-1-yl) methyl]-4-nitro-thieno12,3-c]pyridin-7-yl]morpholine

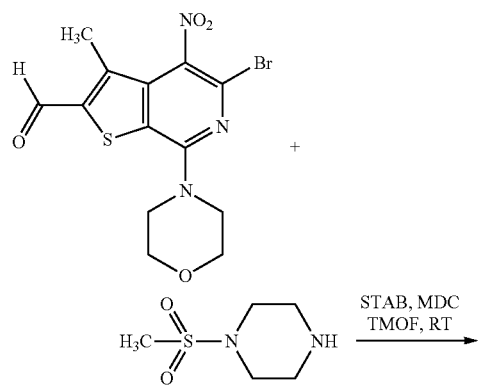

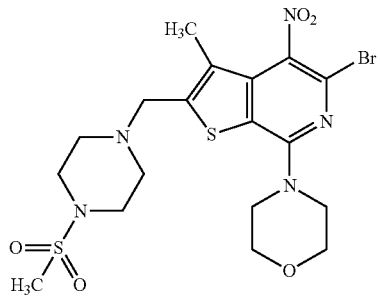

A mixture 500 mg (1.3 mmol) of 5-bromo-3-methyl-7-morpholino-4-nitro-thieno[2,3-c]pyridine-2-carbaldehyde was reacted with 366 mg (2.2 mmol, 1.6 meq) of 1-methylsulfonylpiperazine in the presence of 5.92 g (55.8 mmol, 40 meq) of trimethylorthoformate (TMOF) followed by reduction using 1.37 g (6.5 mmol, 5.0 meq) of sodiumtriacetoxyborohyride (STAB) in methylene chloride at room temperature. The reaction mixture was quenched in water and extracted with methylene chloride. The solvent was removed by distillation and the resulting crude product was purified by column chromatography using ethyl acetate and hexane to afford 600 mg of 4-[5-bromo-3-methyl-2-[(4-methylsulfonylpiperazin-1-yl)methyl]-4-nitro-thieno[2,3-c]pyridin-7-yl]morpholine as yellow colour solid.

$^1$HNMR (400 MHz, CDCl$_3$, δ ppm): 2.07 (s, 3H, CH$_3$); 2.60-2.62 (m, 4H, 2 X CH$_2$); 2.90 (s, 3H, CH$_3$); 3.12-3.13 (m, 4H, 2 X CH$_2$), 3.76 (s, 8H, 4 X CH$_2$); 3.89 (s, 2H, CH$_2$).

EXAMPLE 33

Preparation of 5-[3-methyl-2-[(4-methylsulfonylpiperazin-1-yl)methyl]-7-morpholino-4-nitro-thieno[2,3-c]pyridin-5-yl]pyrimidin-2-amine (compound 9)

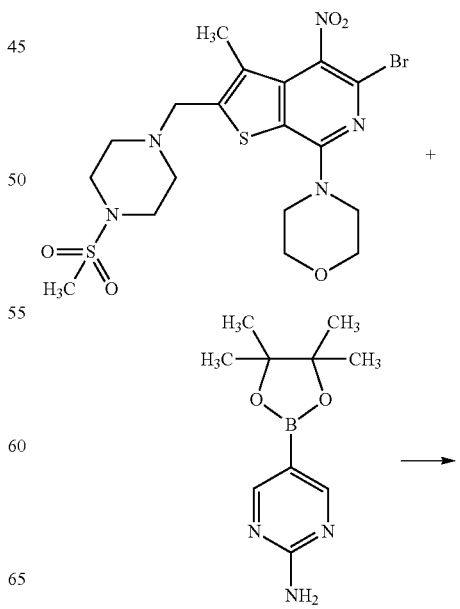

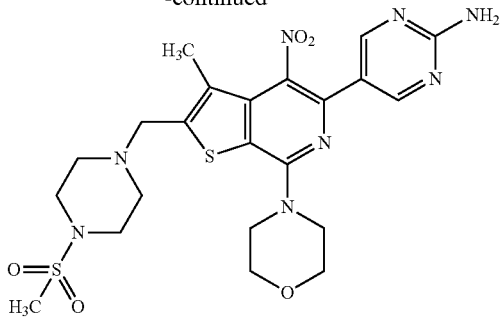

A mixture of 750 mg (14.4 mmol) 4-[5-bromo-3-methyl-2-[(4-methylsulfonylpiperazin-1-yl) methyl]-4-nitro-thieno[2,3-c]pyridin-7-yl]morpholine, 640 mg (28.9 mmol, 2.0 meq) of 5-(4,4,5,5-tetramethyl-1,3,2-dioxaborolan-2-yl)pyrimidin-2-amine, toluene (30 ml), ethanol (15 ml), aq. sodium carbonate (3 ml) and 132 mg (0.13meq) PdCl$_2$(TPP)$_2$ was heated to 115-120° C. in a sealed glass tube for 2.5 h. The reaction mixture was cooled and the solvent were removed by distillation under vacuum to give crude product. The crude product was purified by column chromatography by using a mixture of ethyl acetate, hexane and methanol to afford 500 mg of 5-[3-methyl-2-[(4-methylsulfonylpiperazin-1-yl)methyl]-7-morpholino-4-nitro-thieno[2,3-c]pyridin-5-yl]pyrimidin-2-amine as yellow colour powder.

$^1$HNMR (400 MHz, CDCl$_3$, δ ppm): 2.11 (s, 3H, CH$_3$); 2.60-2.62 (m, 4H, 2 X CH$_2$); 2.90 (s, 3H, CH$_3$); 3.13-3.14 (m, 4H, 2 X CH$_2$), 3.74-3.78 (s, 8H, 4 X CH$_2$); 3.90 (s, 2H, CH$_2$); 8.41 (s, 2H, Ar—H).

EXAMPLE 34

Preparation of 5-(2-amino-pyrimidin-5-yl)-3-methyl-2-[(4-methylsulfonyl piperazin-1-yl)methyl]-7-morpholino-thieno[2,3-c]pyridin-4-amine (compound 10)

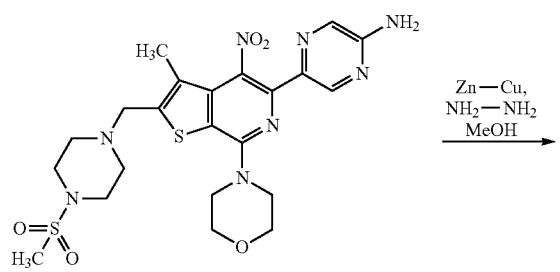

A mixture of 50 mg (0.09 mmol) 5-[3-methyl-2-[(4-methylsulfonylpiperazin-1-yl)methyl]-7-morpholino-4-nitro-thieno[2,3-c]pyridin-5-yl]pyrimidin-2-amine was reduced by using 120 mg (0.9 mmol, 10.0 meq) zinc-copper complex and 80% hydrazine hydrate (2.4 mL) in methanol (5 mL) at 50-55° C. under nitrogen atmosphere for 7 h. The reaction mixture was cooled and solvent was distilled off under vacuum to give crude product. The product was extracted with chloroform (200 mL) and washed with water. The solution was dried over anhydrous sodium sulfate and filtered. The solvent was distilled off by using vacuum to give 20 mg of 5-(2-amino-pyrimidin-5-yl)-3-methyl-2-[(4-methylsulfonylpiperazin-1-yl)methyl]-7-morpholino-thieno[2,3-c]pyridin-4-amine as pale yellow colour solid. The HPLC purity is >95%.

$^1$HNMR (400 MHz, CDCl$_3$, δ ppm): 2.64 (s, 3H, CH$_3$); 2.66-2.68 (m, 4H, 2 X CH$_2$,); 2.81 (s, 3H, CH$_3$); 3.28-3.30 (m, 4H, 2 X CH$_2$), 3.36-3.38 (m, 4H, 2 X CH$_2$); 3.78 (s, 2H, CH$_2$); 3.88-3.90 (m, 4H, 2 X CH$_2$); 4.00 (bs, 2H, NH$_2$, D$_2$O exchangeable); 5.18 (s, 2H, NH$_2$, D$_2$O exchangeable); 8.69 (s, 2H, Ar—H). Mass: 519.6 [M+1]

EXAMPLE 35

Preparation of 5-[3-methyl-2-[(4-methylsulfonylpiperazin-1-yl)methyl]-7-morpholino-4-nitro-thieno[2,3-c]pyridin-5-yl]pyrimidine-2,4-diamine (Compound 11)

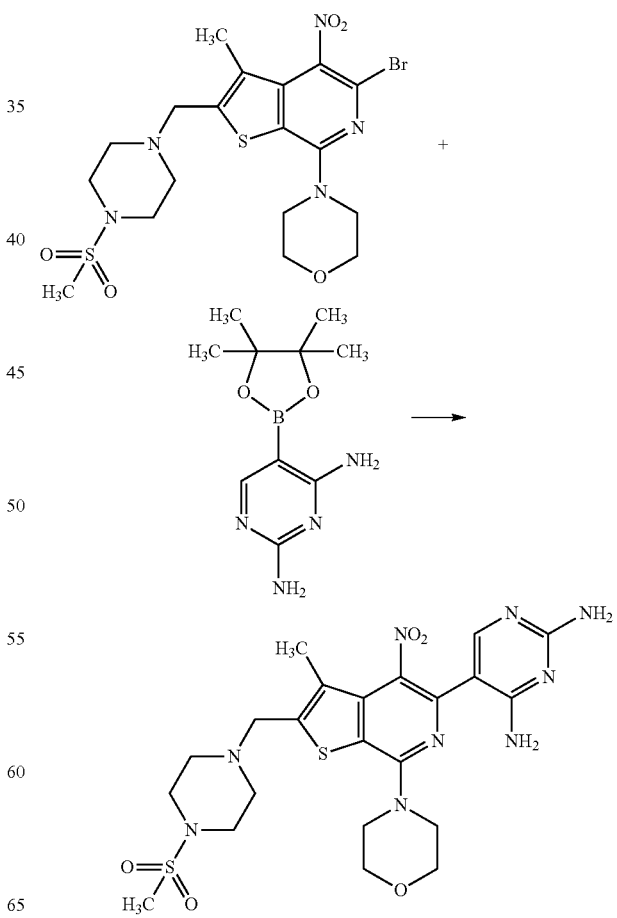

A mixture of 55 mg (0.106 mmol) 4-[5-bromo-3-methyl-2-[(4-methylsulfonylpiperazin-1-yl)methyl]-4-nitro-thieno[2,3-c]pyridin-7-yl]morpholine was condensed with crude 5-(4,4,5,5-tetra methyl-1,3,2-dioxaborolan-2-yl)pyrimidine-2,4-diamine (prepared by reaction of 0.5 g (2, 4-diamino-5-bromopyrimidine and 1.34 g bis(pinacalato)diboron in the presence of $PdCl_2(TPP)_2$ and potassium acetate in 1,4-dioxan), toluene (4 ml), ethanol (4 ml), aq. sodium carbonate (0.4 ml) and 10 mg $PdCl_2(TPP)_2$ was heated to 115-120° C. in a sealed glass tube for 2.5 h. The reaction mixture was cooled and the solvent were removed by distillation under vacuum to give crude product. The crude product was purified by column chromatography by using a mixture of ethyl acetate, hexane and methanol to afford 10 mg of 5-[3-methyl-2-[(4-methylsulfonylpiperazin-1-yl)methyl]-7-morpholino-4-nitro-thieno[2,3-c]pyridin-5-yl]pyrimidine-2,4-diamine as yellow colour solid.

$^1$HNMR (400 MHz, $CDCl_3$, δ ppm): 2.18 (s, 3H, $CH_3$); 2.67-2.69 (m, 4H, 2 X $CH_2$); 2.82 (s, 3H, $CH_3$); 3.29-3.30 (m, 4H, 2 X $CH_2$); 3.72-3.74 (m, 4H, 2 X $CH_2$); 3.82 (s, 2H, $CH_2$); 3.88-3.89 (m, 4H, 2 X $CH_2$); 5.12 (bs, 2H, $NH_2$, $D_2O$ exchangeable); 5.50 (bs, 2H, $NH_2$, $D_2O$ exchangeable); 7.94 (s, 1H, Ar—H). Mass: 564.06 [M+1]; DSC: 249-252° C.

EXAMPLE 36

Preparation of 5-[4-amino-3-methyl-2-[(4-methylsulfonylpiperazin-1-yl)methyl]-7-morpholino-thieno[2,3-c]pyridin-5-yl]pyrimidine-2,4-diamine (compound 12)

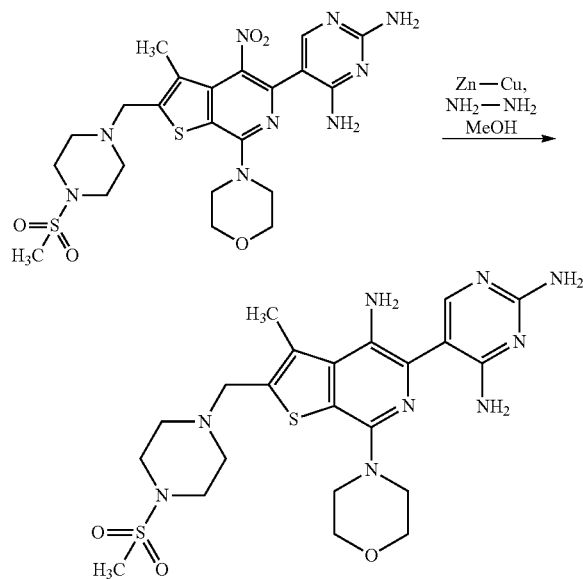

A mixture of 110 mg (0.19 mmol) 5-[3-methyl-2-[(4-methylsulfonylpiperazin-1-yl)methyl]-7-morpholino-4-nitro-thieno [2,3-c]pyridin-5-yl]pyrimidine-2,4-diamine was reduced by using 300 mg (1.95 mmol, 10.0 meq) zinc-copper complex and 80% hydrazine hydrate (6.0 mL) in methanol (20 mL) at 50-55° C. under nitrogen atmosphere for 7h. The reaction mixture was cooled and solvent was distilled off under vacuum to give crude product. The product was extracted with chloroform (200 mL) and washed with water. The solution was dried over anhydrous sodium sulfate and filtered. The solvent was distilled off by using vacuum followed column purification to give 57 mg 5-[4-amino-3-methyl-2 -[(4-methy lsulfonylpiperazin-1-yl)methyl]-7-morpholino-thieno [2,3 -c]pyridin-5-yl]pyrimidine-2,4-diamine as pale yellow colour solid. The HPLC purity is >95%.

$^1$HNMR (400 MHz, $CDCl_3$, δ ppm): 2.63 (s, 3H, $CH_3$); 2.67-2.68 (m, 4H, 2 X $CH_2$,); 2.81 (s, 3H, $CH_3$); 3.30-3.32 (m, 8H, 4 X $CH_2$); 3.78 (s, 2H, $CH_2$); 3.89-3.90 (m, 4H, 2 X $CH_2$); 4.03 (s, 2H, $NH_2$, $D_2O$ exchangeable); 4.84 (s, 2H, $NH_2$, $D_2O$ exchangeable); 5.55 (bs, 2H, $NH_2$, $D_2O$ exchangeable); 8.17 (s, 1H, Ar—H). Mass: 534.2 [M+1]

Biological Testing:

A: In-vitro studies: Compound-1 & 2 are dissolved in cell culture medium and DMSO at a concentration of 10mM for in-vitro studies. The stock solution is further diluted with the same cell culture medium and used in concentrations of 0.01 μm to 10 μm. For the study, the results of which are disclosed here the solid tumor cell lines lung, breast, pancreatic, prostate and glioma.

Cell proliferation by MTT assay was done as follows: 1000 to 10,000 cells were seeded per well in 96-well plate and different concentrations of compound-1 & 2 ranging from 10 μm to 0.1 μm were added in triplicates. After incubating the cells with compound-1 & 2 for the required time period 24-72 hrs, 15 μl of 5 mg/ml MTT was added and incubated for additional 4 hrs at 37° C. and 5% $CO_2$. After 4 hrs, formazan crystals were dissolved in solubilizing buffer overnight at 37° C. Absorbance was measured on Elisa reader at dual wavelength of 570-630-nm. By MTT assay the IC50 values of the compound 1 & 2 are computed. IC 50 values obtained by MTT assay tabulated in table shown in FIG. 1.

B: In vivo studies:

a. MTD (Maximum Tolerated Dose Study in Mice)

The method was carried out as per OECD procedure. The study was carried out using 5 (2 Male+3 Female) Swiss Albino Mice weighing between 18-30 gms. All the animals were fasted for 3 hrs prior to the oral administration of the drug. After preparing the sample administer immediately to their body all the animals according weight. After administration of drug all the animals were observed for ½ hr, 1 hr, 2 hr, 4 hrs and mortality was observed for 14 days. At the end of 14 days all the surviving animals were autopsied and stomach were cut opened and observed for absorption of the drug through the GIT. The result is given in FIG. 1.

COMPOUND 2: MTD>2000 mg.kg, p.o (Single dose 14 days observation)

COMPOUND 1: MTD=500 mg/kg, p.o (Single dose 14 days observation)

b. Antagonism of MIAPaca—2 Induced Tumor in Nude Mice:

This study was carried out with 20 Male Nude Mice. Weighing of Nude Mice were taken initially before inoculation of cell line and made into four groups.

Group-I: Positive control (5 Male)
Group-II: COMPOUND 2 (5 Male) (200 mg/kg, p.o)
Group-III: COMPOUND 1 (5 Male) (50 mg/kg, p.o)
Group-IV: Standard (5 Male) (Erlotinib hydrochloride—50 mg/kg, p.o & Gemcitabine hydrochloride—120 mg/kg, i.p.)

The cell line was inoculated to Nude Mice subcutaneously to the right hind limb flank at a strength of $1 \times 10^7$ cells/0.2 ml. Animals were observed for the appearance of tumor daily. The tumor volume was measured using the formula ½ l×w$^2$ (l=length of tumor & w=width of tumor). When the mean tumor volume was recorded above 400 mm$^3$, the treatment with the above drugs were started. The above drugs were administered orally daily for 30 days, except Gemcitabine hydrochloride was administered on 1st and 3rd day of each week. Weight of Nude Mice was taken daily before dosing and tumor measurement was done on alternative days using digital Vernier caliper. Surviving animals were sacrificed after the dosing is complete for 30 days and organs (tumor with skin and pancreas) were collected.

Mice dead during experimental schedule, the tumor with skin and pancreas were collected and tumor with skin was stored in 10% buffered formalin and pancreas were stored in Bouin's solution. All the organs after collection were sent for histopathology.

The observed results are explained below.

Control: it was seen that the mean tumor area was 33.13mm². Two out of 5 (40%) tumors did not show any invasion into surrounding tissue while an equal no (40%) showed vascular invasion. One tumor showed spread towards the dermis.

COMPOUND 2 (200 mg/kg, p.o): The mean tumor area was 10.90mm². Three out of 5 (60%) tumor were localized and no tumor invasion was seen while remaining (40%) showed vascular invasion.

COMPOUND 1 (50 mg/kg, p.o): The mean tumor area was 8.60mm² and only ⅕ (20%) showed invasion into underlying muscle while remaining 80% showed no much activity.

The results are shown in FIG. 2.

Standard [Erlotinib (50 mg/kg, p.o)+Gemcitabine (120 mg/kg, i.p)]: The mean tumor area was 11.10mm². 1 sample has no tumor presence while 60% of tumor showed no invasion and only 1 (20%) showed vascular invasion.

c. Antagonism of NCI-H292 induced tumor in Nude Mice:

The study was carried out with 15 Nude Mice (8 Male+7 Female).Weighing of Nude Mice were taken initially before inoculation of cell line and made into groups. Grouping as follows:

Group I: Positive control (4 Male+1 Female)

Group II: COMPOUND 2 (2 Male+3 Female) (200 mg/kg, p.o) (shown in FIG. 4)

Group III: COMPOUND 1 (2 Male+3 Female) (50 mg/kg, p.o) (shown in FIG. 3)

The cell line was inoculated to Nude Mice subcutaneously to the right hind limb flank at a strength of 6.25×10⁵ cells/0.2 ml. Animals were observed for the appearance of tumor daily. The tumor volume was measured using the formula ½×w² (l=length of tumor & w=width of tumor).When the mean tumor volume was recorded above 400 mm³, the treatment with the above drugs will be started. The above drugs were administered orally daily for 40 days. Weight of Nude Mice Was taken daily before dosing and tumor measurement was done on alternative days using digital Vernier caliper. Surviving animals were sacrificed after the dosing is complete for 40 days and organs (tumor with skin and Liver) were collected. Mice dead during experimental schedule, the tumor with skin and liver were collected and stored in 10% buffered formalin .All the organs after collection were sent for histopathology.

Histopathological Observations:

Histopathological report suggests that in positive control the subcutaneous tumor with muscle invasion was found to be present in all the animals (5 animals).COMPOUND 2 at the dose level of 200 mg/kg for 7 days treatment showed the clearance of tumor in all the animals (5/5).COMPOUND 1 at the dose level of 50 mg/kg for 15 days showed the clearance of tumor in 80% animals (4/5).Thus suggesting the anti-tumor activity against NCI-H292 (Erlotinib resistant lung cancer).

Advantages:
1. Novel compounds of 7-(morpholinyl)-2-(N-piperazinyl)-methyl thieno [2, 3-c] pyridines of formula-I that are useful in treating cancer diseases in warm blooded species.
2. The process results in providing novel intermediates.
3. Process also results in the preparation of pure grade thieno[2,3-c]pyridine derivatives of formula-I convenient for any scale of operation

We claim:

1. A 7-(Morpholinyl)-2-(N-piperazinyl)methyl thieno[2, 3-c]pyridine compound of Formula-I or a pharmaceutically acceptable salt thereof,

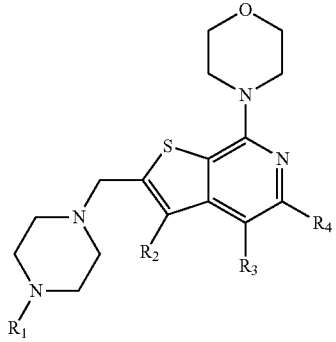

Formula-I wherein:

$R_1$ is H, $C_1$-$C_6$ alkyl, $C_3$-$C_6$ cycloalkyl, —C(O)$R_5$, —S(O)$_2$$R_5$, —C(O)$_2$$R_5$, $C_1$-$C_6$ alkyl substituted with $R_6$, $C_3$-$C_6$ cycloalkyl substituted with $R_6$, aryl, aryl substituted with $R_6$ or heteroaryl substituted with $R_6$;

$R_2$, $R_3$ and $R_4$ are each independently H, —OH, —SH, halo, amino, cyano, -nitro, $C_1$-$C_6$ alkyl, $C_3$-$C_6$ cycloalkyl, aryl, lower alkoxy group, —C(O)$R_5$, —S(O)$_2$$R_5$, —C(O)$_2$$R_5$, —C═C(H)—$R_6$, aminocarbonyl substituted with $R_6$, alkylamino group substituted with $R_6$ and optionally containing $C_3$-$C_6$ cycloalkyl, -alkylaminocarbonyl, arylaminocarbonyl, heteroaryl, heteroaryl optionally substituted with H, amino, aminoalkyl or aminocycloalkyl containing $C_3$-$C_6$ carbon atoms, fused bicyclic or tricyclic heteroaryl containing 1, 2 or 3 heteroatoms such as N, O or S, or aryl optionally substituted with hydroxyl, hydroxylalkyl, amino, aminoalkyl, aminocarbonyl, alkynyl, cyano, halogen, lower alkoxy, aryloxy or $R_6$;

$R_5$ is H, alkyl, amino, aminoalkyl, —N(alk)$_2$, aryl substituted with $R_6$, heteroaryl substituted with $R_6$, fused heteroaryl substituted with $R_6$ or -trifluoromethyl; and $R_6$ is H, hydroxy, halogen, cyano, nitro, amino, $C_1$-$C_6$ alkyl, —N(alk)2, substituted alkyl (CH)0-6, optionally substituted aryl, optionally substituted heteroaryl, optionally substituted aralkyloxy, aryl(hydroxyl)alkyl, aromatic acylamino, arylsulfonylamino, lower alkoxyl aryl sulfonylamino, hydroxyl lower alkoxyl styryl, lower alkoxyl aryloxy, optionally substituted arylalkenyl, heteroarylalkenyl, heteroarylalkynyl, aromatic acyl alkynyl, optionally N-substituted amino lower alkyl, arylamino or arylalkylamino.

2. A compound according to claim 1 or a pharmaceutically acceptable salt thereof, which compound is:

i) 5-[3-methyl-2-[(4-methylsulfonylpiperazin-1-yl) methyl]-7-morpholino-thieno[2,3-c]pyridin-5-yl]pyrimidin-2-amine;
ii) 5-[2-[(4-methylsulfonylpiperazin-1-yl)methyl]-7-morpholino-thieno[2,3-c]pyridin-5-yl]pyrimidin-2-amine;
iii) 4-[5-(1H-indazol-4-yl)-2-[(4-methylsulfonylpiperazin-1-yl)methyl]thieno[2, 3-c]pyridin-7-yl]morpholine;
iv) [3-[2-[(4-methylsulfonylpiperazin-1-yl)methyl]-7-morpholino-thieno[2,3-c]pyridin-5-yl]phenyl]methanol;
v) 3-[2-[(4-methylsulfonylpiperazin-1-yl)methyl]-7-morpholino-thieno[2,3-c]pyridin-5-yl]aniline;
vi) 4-[5-(1H-indazol-4-yl)-3-methyl-2-[(4-methylsulfonylpiperazin-1-yl)methyl]thieno[2,3-c]pyridin-7-yl] morpholine;
vii) [3-[3-methyl-2-[(4-methylsulfonylpiperazin-1-yl) methyl]-7-morpholino-thieno[2,3-c]pyridin-5-yl]phenyl]methanol;
viii) 3-[3-methyl-2-[(4-methylsulfonylpiperazin-1-yl) methyl]-7-morpholino-thieno[2,3-c]pyridin-5-yl]aniline;
ix) 5-[3-methyl-2-[(4-methylsulfonylpiperazin- 1-yl) methyl]-7-morpholino-4-nitro-thieno[2,3 -c]pyridin-5-yl]pyrimidin-2-amine;
x) 5-(2-amino-pyrimidin-5-yl)-3-methyl-2-[(4-methylsulfonylpiperazin-1-yl)methyl]-7-morpholino-thieno[2,3-c]pyridin-4-amine;
xi) 5-[3-methyl-2-[(4-methylsulfonylpiperazin-1-yl) methyl]-7-morpholino-4-nitro-thieno[2,3-c]pyridin-5-yl]pyrimidin-2,4-diamine; or
xii) 5-[4-amino-3-methyl-2-[(4-methylsulfonylpiperazin-1-yl)methyl]-7-morpholino-thieno[2,3-c]pyridin-5-yl] pyrimidine-2,4-diamine.

3. A compound according to claim 1, which compound is a compound of Formula-II,

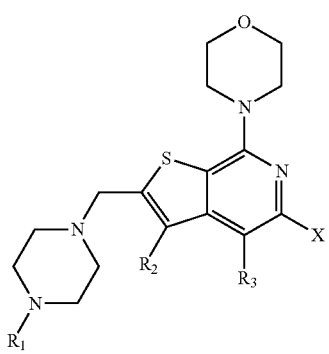

Formula-II wherein X is a halogen.

4. A compound according to claim 3, which compound is:
i) 4-[5-bromo-3-methyl-2-[(4-methylsulfonylpiperazin-1-yl)methyl]-4-nitro-thieno[2,3-c]pyridin-7-yl]morpholine;
ii) 4-[5-bromo-2-[(4-methylsulfonylpiperazin-1-yl) methyl]thieno[2,3-c]pyridin-7-yl]morpholine; or
iii) 4-[5-bromo-3-methyl-2-[(4-methylsulfonylpiperazin-1-yl)methyl]thieno[2,3-c]pyridin-7-yl]morpholine.

5. A pharmaceutical composition comprising:
(a) a therapeutically effective amount of a 7-(Morpholinyl)-2-(N-piperazinyl)methyl thieno[2,3-c]pyridine compound of Formula-I or a pharmaceutically acceptable salt thereof,

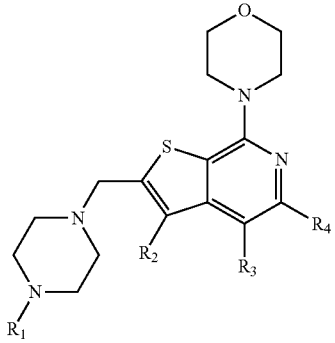

Formula-I wherein:

$R_1$ is H, $C_1$-$C_6$ alkyl, $C_3$-$C_6$ cycloalkyl, —C(O)$R_5$, —S(O)$_2R_5$, —C(O)$_2R_5$, $C_1$-$C_6$ alkyl substituted with $R_6$, $C_3$-$C_6$ cycloalkyl substituted with $R_6$, aryl, aryl substituted with $R_6$ or heteroaryl substituted with $R_6$;

$R_2$, $R_3$ and $R_4$ are each independently H, —OH, —SH, halo, amino, cyano, -nitro, $C_1$-$C_6$ alkyl, $C_3$-$C_6$ cycloalkyl, aryl, lower alkoxy group, —C(O)$R_5$, —S(O)$_2R_5$, —C(O)$_2R_5$, —C=C(H)-$R_6$, aminocarbonyl substituted with $R_6$, alkylamino group substituted with $R_6$ and optionally containing $C_3$-$C_6$ cycloalkyl, -alkylaminocarbonyl, arylaminocarbonyl, heteroaryl, heteroaryl optionally substituted with H, amino, aminoalkyl or aminocycloalkyl containing $C_3$-$C_6$ carbon atoms, fused bicyclic or tricyclic heteroaryl containing 1, 2 or 3 heteroatoms such as N, O or S, or aryl optionally substituted with hydroxyl, hydroxylalkyl, amino, aminoalkyl, aminocarbonyl, alkynyl, cyano, halogen, lower alkoxy, aryloxy or $R_6$;

$R_5$ is H, alkyl, amino, aminoalkyl, —N(alk)$_2$, aryl substituted with $R_6$, heteroaryl substituted with $R_6$, fused heteroaryl substituted with $R_6$ or -trifluoromethyl;

$R_6$ is H, hydroxy, halogen, cyano, nitro, amino, $C_1$-$C_6$ alkyl, —N(alk)$_2$, substituted alkyl (CH)$_{0-6}$, optionally substituted aryl, optionally substituted heteroaryl, optionally substituted aralkyloxy, aryl(hydroxyl)alkyl, aromatic acylamino, arylsulfonylamino, lower alkoxyl aryl sulfonylamino, hydroxyl lower alkoxyl styryl, lower alkoxyl aryloxy, optionally substituted arylalkenyl, heteroarylalkenyl, heteroarylalkynyl, aromatic acyl alkynyl, optionally N-substituted amino lower alkyl, arylamino or arylalkylamino; and (b) a pharmaceutically acceptable carrier, diluent or vehicle.

6. A method for treating cancer, wherein the cancer is lung cancer, pancreatic cancer, prostate cancer, breast cancer, brain cancer or ovarian cancer, said method comprising: administering to a human a therapeutically effective amount of a 7-(Morpholinyl)-2-(N-piperazinyl)methyl thieno[2,3-c] pyridine compound of Formula-I or a pharmaceutically acceptable salt thereof,

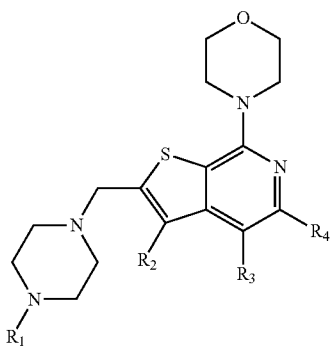

Formula-I wherein:
R1 is H, C1-C6 alkyl, C3-C6 cycloalkyl, —C(O)R5, —S(O)2R5, —C(O)2R5,
C1-C6 alkyl substituted with R6, C3-C6 cycloalkyl substituted with R6, aryl, aryl substituted with R6 or heteroaryl substituted with R6;
$R_2$, $R_3$ and $R_4$ are each independently H, —OH, —SH, halo, amino, cyano, -nitro, $C_1$-$C_6$ alkyl, $C_3$-$C_6$ cycloalkyl, aryl, lower alkoxy group, —C(O)$R_5$, —S(O)$_2R_5$, —C(O)$_2R_5$, —C≡C(H)—$R_6$, aminocarbonyl substituted with $R_6$, alkylamino group substituted with $R_6$ and optionally containing $C_3$-$C_6$ cycloalkyl, -alkylaminocarbonyl, arylaminocarbonyl, heteroaryl, heteroaryl optionally substituted with H, amino, aminoalkyl or aminocycloalkyl containing $C_3$-$C_6$ carbon atoms, fused bicyclic or tricyclic heteroaryl containing 1, 2 or 3 heteroatoms such as N, O or S, or aryl optionally substituted with hydroxyl, hydroxylalkyl, amino, aminoalkyl, aminocarbonyl, alkynyl, cyano, halogen, lower alkoxy, aryloxy or $R_6$;

$R_5$ is H, alkyl, amino, aminoalkyl, —N(alk)$_2$, aryl substituted with $R_6$, heteroaryl substituted with $R_6$, fused heteroaryl substituted with $R_6$ or -trifluoromethyl;

$R_6$ is H, hydroxy, halogen, cyano, nitro, amino, $C_1$-$C_6$ alkyl, —N(alk)$_2$, substituted alkyl (CH)$_{0-6}$, optionally substituted aryl, optionally substituted heteroaryl, optionally substituted aralkyloxy, aryl(hydroxyl)alkyl, aromatic acylamino, arylsulfonylamino, lower alkoxyl aryl sulfonylamino, hydroxyl lower alkoxyl styryl, lower alkoxyl aryloxy, optionally substituted arylalkenyl, heteroarylalkenyl, heteroarylalkynyl, aromatic acyl alkynyl, optionally N-substituted amino lower alkyl, arylamino or arylalkylamino.

7. The method according to claim 6 which comprises orally, parenterally or rectally administering to said human an effective anticancer amount of the 7-(Morpholinyl)-2-(N-piperazinyl)methyl thieno[2,3-c]pyridine compound of Formula-I or a pharmaceutically acceptable salt thereof.

\* \* \* \* \*